United States Patent [19]
Smith et al.

[11] Patent Number: 6,127,131
[45] Date of Patent: Oct. 3, 2000

[54] DNA ENCODING A GLYCINE TRANSPORTER AND USES THEREOF

[75] Inventors: Kelli E. Smith, Wayne; Laurence A. Borden, Hackensack; Theresa Branchek, Teaneck; Paul R. Hartig, Princeton, all of N.J.; Richard L. Weinshank, New York, N.Y.

[73] Assignee: Synaptic Pharmaceutical Corporation, Paramus, N.J.

[21] Appl. No.: 09/084,813

[22] Filed: May 26, 1998

Related U.S. Application Data

[60] Division of application No. 08/240,783, filed as application No. PCT/US92/09662, Nov. 12, 1991, Pat. No. 5,756,348, which is a continuation-in-part of application No. 07/791,927, Nov. 12, 1991, abandoned.

[51] Int. Cl.$^7$ .......................... G01N 33/53; G01N 33/567
[52] U.S. Cl. .............................. 435/7.1; 435/7.2; 435/7.21
[58] Field of Search ........................... 435/7.1, 7.2, 7.21; 436/501

[56] References Cited

U.S. PATENT DOCUMENTS 5,225,323  7/1993  Lam et al. .
5,421,185  6/1995  Lam et al. .

FOREIGN PATENT DOCUMENTS 5350490  6/1990  Australia .
9006047  6/1990  WIPO .

OTHER PUBLICATIONS

Blakely, R.D., "Distinct, Developmentally Regulated Brain nRNAs Directed the Synthesis of Neurotransmitter Transporter" *J. of Neurochem.* (1991) 56(3): 860–871.

Blakely, R.D., et al., "Cloning and expression of a functional serotonin transporter from rat brain" *Nature* (1991) 354: 66–70.

Corcuera–Lopez, B., et al., "Purification of the Sodium and Chloride coupled Glycine transporter from central nervous system" *J. Biol. Chem.* 266(36): 24809–24814, 1991.

Guastella, J., et al., "Cloning and Expression of A Rat Brain GABA Transporter" *Science* (1990) 249: 1303–1306.

Guastella, J., et al., "Cloning, expression, and localization of a rat brain high–affinity glycine transporter" *PNAS, USA* (1992) 89: 7189–7193.

Hoffman, B.J., et al., "Cloning of a Serotonin Transporter Affected by Antidepressants" *Science* (1991) 254: 578–579.

Kilty, J.E., et al., "Cloning and Expression of a Cocaine–Sensitive Rat Dopamine Receptor" *Science* (1991) 254: 578–579.

Liu, Q.R., et al., "A family of genes encoding neurotransmitter transporters" *PNAS* (1992) 89: 6639–6643.

Liu, Q.R., et al., "Cloning and expression of a glycine transporter from mouse brain" *FEBS Letters* (1992) 305(2): 110–114.

Mayser, W., et al., "Isolation of cDNAs encoding a novel member of the neurotransmitter transporter gene family" *FEBS Letters* (1991) 295:(1) (2) (3): 203–206.

Pacholczyk, T., et al., "Expression cloning of a cocaine and antidepressant sensitive human noradrenaline transporter" *Nature* (1991) 350: 350–354.

Sambrook, J., et al., "Molecular Cloning, A Laboratory Manual" Cold Spring Harbor Laboratory Press, New York (1989) 16.68–16.81.

Scangos, G., et al., "Advances in Genetics" *Academic Press* (1987) 24: 285–322.

Shimada, S., et al., "Cloning and Expression of a Cocaine Sensitive Dopamine Transporter Complementary DNA" *Science* (1991) 254: 576–578.

Smith, K.E., et al., "Cloning and expression of a Glycine Transporter reveal colocalization with NMDA receptor" *Neuron* (1992) 8(5): 927–935.

Zhao, Z.Y., et al., "Isolation of Distantly Related Members in a multigene Family Using the Polymerase Chain Reaction Technique" *Biochem. and Biophys. Res. Comm.* (1990) 167(1): 174–182.

Rine, J., *Methods in Enzymology* (1991) 194: 239–251.

*Primary Examiner*—Marianne P. Allen
*Attorney, Agent, or Firm*—John P. White; Cooper & Dunham LLP

[57] ABSTRACT

This invention provides isolated nucleic acid molecules encoding a mammalian glycine transporter, isolated nucleic acid molecules encoding a human glycine transporter, isolated proteins which are mammalian glycine transporter proteins, isolated proteins which are human glycine transporter proteins, vectors comprising isolated nucleic acid molecules encoding a mammalian or a human glycine transporter, mammalian cells comprising such vectors, antibodies directed to a mammamlian glycine transporter, antibodies directed to a human glycine transporter, nucleic acid probes useful for detecting nucleic acid encoding mammalian glycine transporter, nucleic acid probes useful for detecting nucleic acid encoding human glycine transporter, antisense oligonucleotides complementary to any sequences of a nucleic acid molecule which encodes a mammalian glycine transporter, antisense oligonucleotides complementary to any sequences of a nucleic said molecule which encodes a human glycine transporter, pharmaceutical compounds related to mammalian glycine transporter and non-human transporter, pharmaceutical compounds related to human glycine transporter and nonhuman transgenic animals which express DNA encoding a normal or a mutant mammalian or human glycine transorter. This invention also provides methods for determining ligand binding, detecting expression, drug screening, and treatments for alleviating abnormalities associated with mammalian glycine transporter. This invention further provides methods for determining ligand binding, detecting expression, drug screening, and treatments for alleviating abnormalities associated with human glycine transporter.

8 Claims, 22 Drawing Sheets

FIGURE 1A

```
        -50                 -30                 -10
GGAGCTGGCAGAGGTGTGAATGAGCCGGCTGAGACACTCGTGCTTTGAGTGCTCTTCCAG 10                  30                  50
GATGGCTGTGGCTCACGGACCTGTGGCCCACCCTCTTCCCCAGAACAGAATGGTGCTGTGCC
 M  A  V  A  H  G  P  V  A  T  S  S  P  E  Q  N  G  A  V  P 70                  90                 110
CAGCGAGGCCACCAAGAAGGACCAGAACCTCACACGGGGCAACTGGGGCAACCAGATCGA
 S  E  A  T  K  K  D  Q  N  L  T  R  G  N  W  G  N  Q  I  E 130                 150                 170
GTTTGTACTGACGAGCGTGGGCTATGCCGTGGGCCTGGGCAATGTGTGGCGTTTCCCATA
 F  V  L  T  S  V  G  Y  A  V  G  L  G  N  V  W  R  F  P  Y 190                 210                 230
CCTCTGCTATCGCAACGGGGGAGGCGCCTTCATGTTCCCTACTTCATCATGCTGGTCTT
 L  C  Y  R  N  G  G  G  A  F  M  F  P  Y  F  I  M  L  V  F
```

FIGURE 1B

```
        250              270              290
         •                •                •
CTGCGGCCATTCCTCTCTCTTCATGGAGCTCTCCTTCGGCCAGTTGCAAGCCAGGGCTG
 C  G  I  P  L  F  F  M  E  L  S  F  G  Q  F  A  S  Q  G  C 310              330              350
         •                •                •
CCTGGGGGTCTGGAGGATCAGCCCCATGTTCAAAGGCGTGGGCTATGGTATGATGGTGGT
 L  G  V  W  R  I  S  P  M  F  K  G  V  G  Y  G  M  M  V  V 370              390              410
         •                •                •
GTCCACGTACATCGGTATCTACTACAACGTGGTCATCTGCATCGCCTTCTACTACTTCTT
 S  T  Y  I  G  I  Y  Y  N  V  V  I  C  I  A  F  Y  Y  F  F 430              450              470
         •                •                •
CTCGTCCATGACGCATGTGCTGCCCTGGGCTTACTGCAATAATCCCTGGAACACACCCGA
 S  S  M  T  H  V  L  P  W  A  Y  C  N  N  P  W  N  T  P  D 490              510              530
         •                •                •
CTGTGCCGGTGTGCTGGATGCTTCCAATCTCACCAATGGCTCCCGGCCCACTGCCCTGTC
 C  A  G  V  L  D  A  S  N  L  T  N  G  S  R  P  T  A  L  S
```

FIGURE 1C

```
550                        570                        590
  .                          .                          .
TGGCAACCTGTCTCACCTGTTCAACTACACCTTGCAAAGGACCAGCCCCAGTGAGGAGTA
 G  N  L  S  H  L  F  N  Y  T  L  Q  R  T  S  P  S  E  E  Y 610                        630                        650
  .                          .                          .
CTGGAGGCTGTATGTGCTGAAGCTGTCGGATGACATTGGAGATTTTGGAGAAGTGCGGCT
 W  R  L  Y  V  L  K  L  S  D  D  I  G  D  F  G  E  V  R  L 670                        690                        710
  .                          .                          .
TCCTCTCCTAGGCTGCCTTGGCGTCTCCTGGGTCGTTGTCTTCCTGTGCCTCATTCGAGG
 P  L  L  G  C  L  G  V  S  W  V  V  V  F  L  C  L  I  R  G 730                        750                        770
  .                          .                          .
AGTCAAGTCTTCAGGGAAAGTGGTGTACTTCACGGCCACATTTCCCTATGTGGTGCTGAC
 V  K  S  S  G  K  V  V  Y  F  T  A  T  F  P  Y  V  V  L  T 790                        810                        830
  .                          .                          .
CATTCTGTTTGTTCGTGGAGTGACCCTGGAAGGAGCCTTCACGGGTATCATGTACTACCT
 I  L  F  V  R  G  V  T  L  E  G  A  F  T  G  I  M  Y  Y  L
```

FIGURE 1D

```
       850              870              890
        .                .                .
GACCCCAAAGTGGGAGACAAGATCCTGGAGGCCAAGGTGTGGGGGGATGCAGCCTCTCAGAT
 T  P  K  V  G  D  K  I  L  E  A  K  V  W  G  D  A  A  S  Q  I 910              930              950
        .                .                .
CTTCTATTCCCTGGGCTGTGCATGGGGTGGCCTCATCACCATGGCATCCTACAACAAATT
 F  Y  S  L  G  C  A  W  G  G  L  I  T  M  A  S  Y  N  K  F 970              990             1010
        .                .                .
CCACAACAACTGCTACCGGGACAGCGTCATCATCAGCATCACCAATTGTGCTACCAGTGT
 H  N  N  C  Y  R  D  S  V  I  I  S  I  T  N  C  A  T  S  V 1030             1050             1070
        .                .                .
CTATGCTGGCTTCGTCATCTTCTCTATCCTAGGCTTCATGGCCAATCACCTGGGTGTGGA
 Y  A  G  F  V  I  F  S  I  L  G  F  M  A  N  H  L  G  V  D 1090             1110             1130
        .                .                .
TGTGTCTCGGGTGGCAGACCACGGGCCCGGGCTAGCTTCGTGGCTTACGTGCCTGAGGCTCT
 V  S  R  V  A  D  H  G  P  G  L  A  F  V  A  Y  P  E  A  L
```

FIGURE 1E

```
        1150                    1170                    1190
         ·                       ·                       ·
CACACTGCTGCTTCCCATCTCCCCGCCTCTGGTCCTTGTGTTTTCTTCATGCTCATCCTGCT
 T  L  L  P  I  S  P  L  W  S  L  L  F  F  F  M  L  I  L  L
        1210                    1230                    1250
         ·                       ·                       ·
GGGACTCGGTACTCAGTTCTGCCTCCTGGAGACCCTAGTCACTGCCATTGTGGATGAGGT
 G  L  G  T  Q  F  C  L  L  E  T  L  V  T  A  I  V  D  E  V
        1270                    1290                    1310
         ·                       ·                       ·
GGGGAATGAGTGGATTCTGCAGAAGAAGACCTACGTGGTGACCCTTGGTGTGGCTGTGGCTGG
 G  N  E  W  I  L  Q  K  K  T  Y  V  V  T  L  G  V  A  V  A  G
        1330                    1350                    1370
         ·                       ·                       ·
CTTCTTGCTGGGTATCCCTCTTACCAGCCAGGGCATCTACTGGCTTCTGCTGTTGATGGA
 F  L  L  G  I  P  L  T  S  Q  A  G  I  Y  W  L  L  L  M  D
        1390                    1410                    1430
         ·                       ·                       ·
CAACTACGCAGCCAGCTTCTCCCTGGTTGTCATCTCCTGCATCATGTGCGTGTCCATCAT
 N  Y  A  A  S  F  S  L  V  V  I  S  C  I  M  C  V  S  I  M
```

FIGURE 1F

```
            1450                     1470                      1490
             .                        .                         .
GTATATCTATGGGCACCGGAACTACTTCCAGGACATTCAGATGATGCTGGGGTTCCCACC
 Y  I  Y  G  H  R  N  Y  F  Q  D  I  Q  M  M  L  G  F  P  P 1510                     1530                      1550
             .                        .                         .
GCCTCTCTTCTTCCAGATCTGTGGCGTTTGTCTCTCCCACTATCATCTTTTTCATTCT
 P  L  F  F  Q  I  C  W  R  F  V  S  P  T  I  I  F  F  I  L 1570                     1590                      1610
             .                        .                         .
CATCTTCACGGTGTGATCCAGTACCGGCCAATCACTTACAACCACTACCCAGGCTG
 I  F  T  V  I  Q  Y  R  P  I  T  Y  N  H  Y  P  G  W 1630                     1650                      1670
             .                        .                         .
GGCTGTGGCCATCGGCTTCCTCATGGCTTTGTCGTCATCTGCATCCCATTGTACGC
 A  V  A  I  G  F  L  M  A  L  S  S  V  I  C  I  P  L  Y  A 1690                     1710                      1730
             .                        .                         .
ATTGTTCCAGCTCTGCCGCACAGATGGGGACACTTCTTCAGCGTTTGAAAATGCCAC
 L  F  Q  L  C  R  T  D  G  D  T  L  L  Q  R  L  K  N  A  T
```

FIGURE 1G

```
              1750                    1770                    1790
                 .                       .                       .
AAAGCCAAGCAGAGACTGGGGGCCCTGCCCTCCTGGAGCACCGGACTGGGCGCTATGCCCC
 K  P  S  R  D  W  G  P  A  L  L  E  H  R  T  G  R  Y  A  P 1810                    1830                    1850
                 .                       .                       .
CACTACAACCCCCTCTCCTGAAGATGGGTTTGAGGTTCAGCCACTGCACCCGGACAAGGC
 T  T  P  S  P  E  D  G  F  E  V  Q  P  L  H  P  D  K  A 1870                    1890                    1910
                 .                       .                       .
CCAGATCCCCATCGTGGGCAGTAACGGCTCCAGCCGCCTCCAGGACTCCCGGATATGAGC
 Q  I  P  I  V  G  S  N  G  S  S  R  L  Q  D  S  R  I  *

1930                    1950                    1970
                 .                       .                       .
ACAGTTGTTGCAAGGGGAGAAGCCCCACCCCAACCCCTTGCTCCTACCACAGAGACTGAGGA 1990                    2010                    2030
                 .                       .                       .
GGTGGTGGACCGGTGTGACTGCCTGCCCCATCATGCCCTGGCCAGGGTGGCTGCTGTCAC

2050
                 .
CTTGGCCACCACTGCTCATGT
```

FIGURE 2A

```
                                                                                              26
                        MATDNSKVADGQISTEVS.EAPV              MAVAHGPVATSSPEQNGAVPSEATKK        38
Glycine                 MLLARMNPQVQPENNGADTGPEQPLRARKTAELLVVKERNGVQCLLA...KA                   50
Gaba
Norepi                                                                  ...APRD
                                                 I
                        DQNLTRGNNGNQIEFVLLTSVGTAVGLGNVWRFPYLCYRNGGAFMFPYFI                     76
Glycine                 GDLPDRDTWKGRFDFLMSCVGYAIGLGNVWRFPYLCGKNGGAFLIPYFL                      88
Gaba                    GDAQPRETNGKKIDFLLESVGFAVDLANVWRFPYLCYKNGGAFLIPYTL                     100
Norepi
                             II
                        MLVFCGIPLFMELSFGQFASQCCLGVNRISPMFKGVGMHVSTFIG.I                      126
Glycine                 TLIFAGVPLFLLECSLGQYTSIGGLGVWKLAPMFKGVGLAAAVLSFWLN.                     138
Gaba                    FLITAGMPLFYMELALGQYNREGAATVWKICPFFKGVGYAVILIALYVGF                    150
Norepi
                                                              III
                        YYNVICIAFYYFFSSMTHVLPWAYCNNPWNTPDCAGVLDASNLTNGSRP..                   176
Glycine                 YVIISWAITYLYNSFITTLPWKQCDNPWN...TD....RCFSNYS..                      178
Gaba                    YYNVIIAWSLYYLFSSFTLNLPWTDCGHTWNSPNCTD....PKLLHGS..                   194
Norepi
```

```
                        IX
Glycine  I L Q K K T Y V T L G V A V A G F L L G I P L T S Q A G T Y W L L L M D N Y . A A S F S L V V I S C  473
Gaba     R N R R E L F . I A A C I V S Y L I G L S N I T G G G I V F K L F D Y L S A S G M S L F L V F  465
Norepi   K R H R K L F . T F G V T F S T F L L A L F C I T K G G I E V L T L L D T F . A A G T S I L F A V L  486
                                           X
Glycine  I M C V S T M Y I Y G H R N Y F Q D I Q M L L G F P P P L F F Q I C W R F V S P T F I F I L I F T  523
Gaba     F E C V S I S W F Y G V N R F Y D N I Q E M V G S R P C I W W K L C W S F F T D I I V A G V F L F S  515
Norepi   M E A I G V S W F I G V D R F S N D Q Q M W E R D G L Y W R L E W K F V S R D A F L L E V V V V S  536
                                                                      XI
Glycine  V I G Y R P I T N H T Q Y R G N A V A I D F L M A L S S V I C F L T A L F Q L C R T D G D T L L  573
Gaba     A V Q M T P L H G S T V F P K N G Q V G V G W M A L S M V L I P G Y M A Y M F L T L K G . S L K  564
Norepi   I I N F K P L L D D Y I F P P W A N W V G W G I A L S S M V L V P I Y V I Y K F L S T Q G . S L W  585
                             XII
Glycine  Q R E K N A T K P S R D W G P A L L E H R T G R Y A P T T T P S P E D G F E V Q P L H P D K A Q I P  623
Gaba     Q R L Q V M I Q P . S E . . D I V R P E N G P E Q P Q A G S S A S K E A Y I . . . . . . . . .  599
Norepi   E R L A Y G I T P E N E . . H H L L V A Q R D I R Q F Q L Q H W L A I . . . . . . . . . . .  617

Glycine  I V G S N G S S R L Q D S R I  638
Gaba     . . . . . . . . . . . . . . .  599
Norepi   . . . . . . . . . . . . . . .  617
```

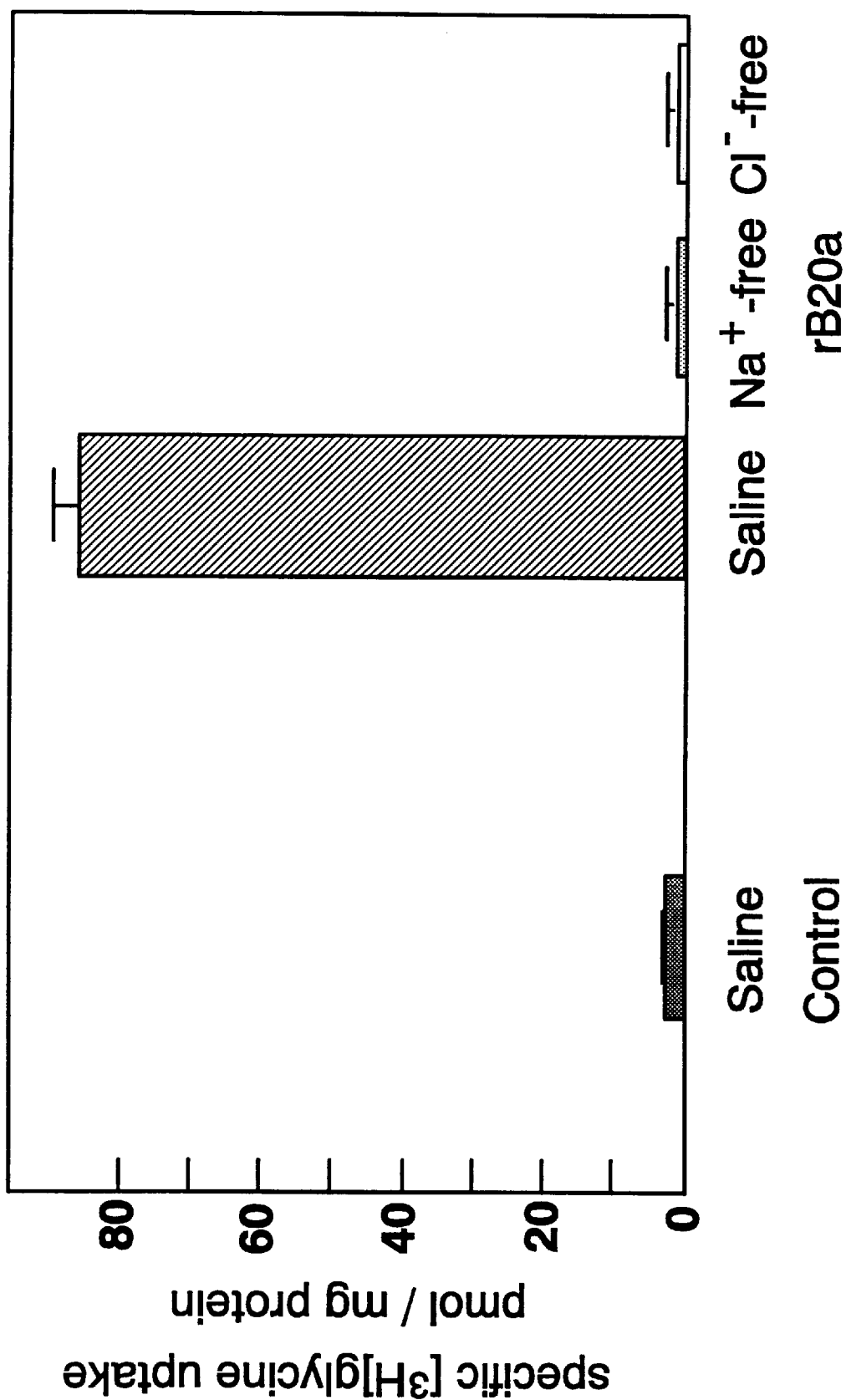

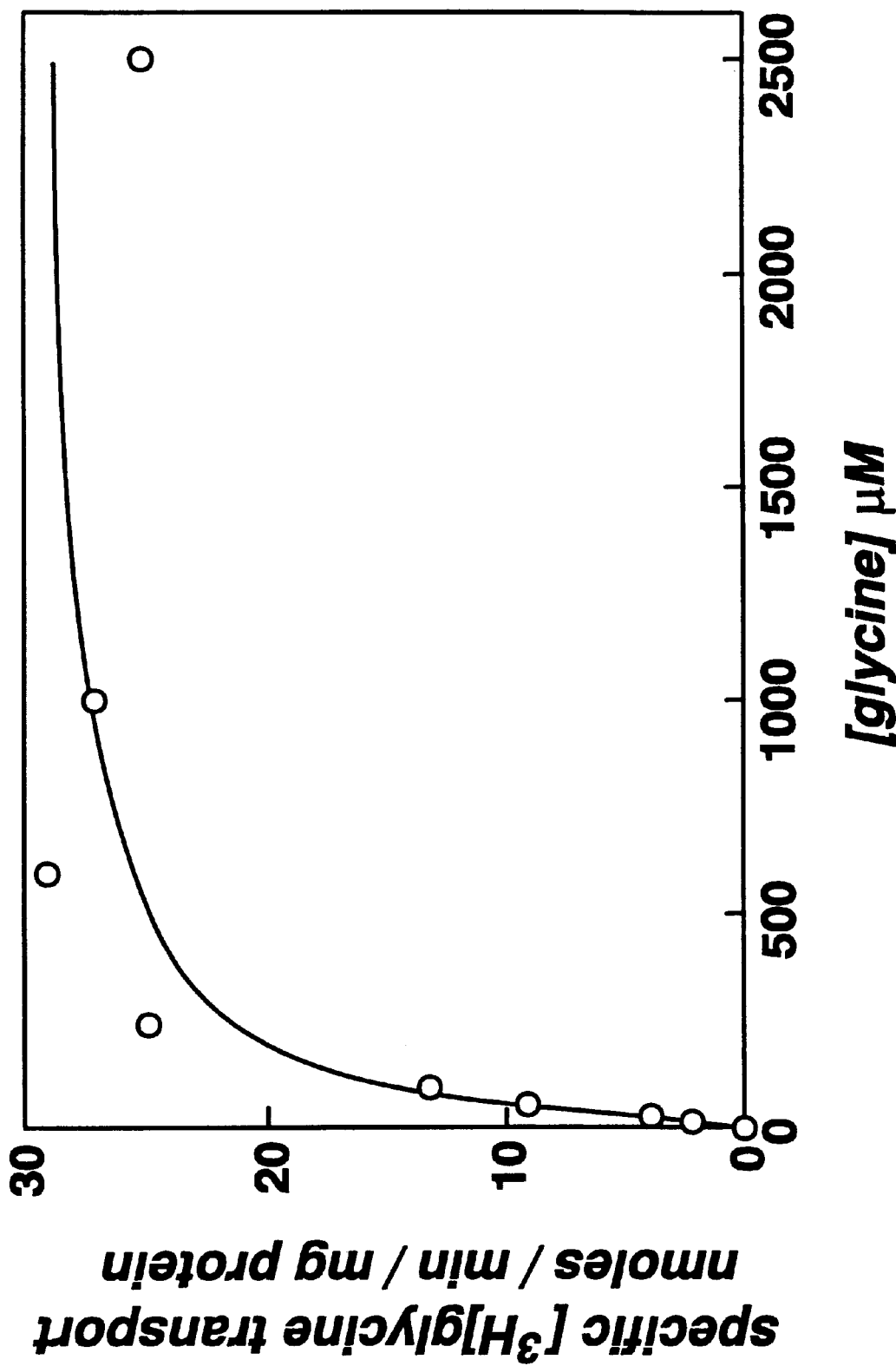

FIGURE 7A

```
-40                    -20                      0
GGCAGGGGGATGCGTCAGTGTCGCGCTGGAGCTGGCAGAGGTGTGAATGAGCGGGGAGAC
                                              M  S  G  G  D 20                     40                     60
GGCGGGCTGCGATCGCTCGCCCCAGGATGGCCGCGGCTCATGGACCCTGTGCCCCCTCT
T  R  A  A  I  A  R  P  R  M  A  A  A  H  G  P  V  A  P  S 80                    100                    120
TCCCCAGAACAGAATGTGCTGTGCCCAGCCGAGCCACCAAGAGGACCAGAACCTCAAA
S  P  E  Q  N  G  A  V  P  S  E  A  T  K  R  D  Q  N  L  K 140                    160                    180
CGGGGCAACTGGGGCAACCAGATCGAGTTTGTACTGACGAGCGTGGGCTATGCCGTGGGC
R  G  N  W  G  N  Q  I  E  F  V  L  T  S  V  G  Y  A  V  G 200                    220                    240
CTGGGCAATGTCTGGCGCTTCCCATACCTCTGCTATCGCAACGGGGAGGCGCCTTCATG
L  G  N  V  W  R  F  P  Y  L  C  Y  R  N  G  G  G  A  F  M
```

FIGURE 7B

```
                              280                    300
TTCCCTACTTCATCATGCTCATCTTCTGCGGGATCCCCCTCTTCTTCATGGAGCTCTCC
 F  P  Y  F  I  M  L  I  F  C  G  I  P  L  F  F  M  E  L  S
                              340                    360
TTCGGCCAGTTTGCAAGCCAGGGGTGCCTGGGGTCTGGAGGATCAGCCCCATGTTCAAA
 F  G  Q  F  A  S  Q  G  C  L  G  V  W  R  I  S  P  M  F  K
                              400                    420
GGAGTGGGCTATGGTATGATGGTTGTCCACCTACATCGGCATCTACTACAATGTGGTC
 G  V  G  Y  G  M  M  V  V  S  T  Y  I  G  I  Y  Y  N  V  V
                              460                    480
ATCTGCATCGCCTTCTACTACTTCTCTTCTGTCCATGACGCCACGTGCTGCCTGGGCTAC
 I  C  I  A  F  Y  Y  F  S  S  M  T  H  V  L  P  W  A  Y
                              520                    540
TGCAATAACCCCTGGAACACGCATGACTGCGCCGGTGTACTGGACGCCTCCAACCTCACC
 C  N  N  P  W  N  T  H  D  C  A  G  V  L  D  A  S  N  L  T
```

FIGURE 7C

```
         560               580                600
          .                 .                  .
AATGGCTCTCGGCCAGCCGCCCTTGCCCAGCAACCCTCTCCCACCTGCTCAACCACAGCCTC
 N  G  S  R  P  A  A  L  P  S  N  L  S  H  H  L  N  H  S  L 620               640                660
          .                 .                  .
CAGAGGACCAGCCCCAGCGAGGAGTACTGGAGGCTGTACGTGGTGAAGCTGTCAGATGAC
 Q  R  T  S  P  S  E  E  Y  W  R  L  Y  V  V  K  L  S  D  D 680               700                720
          .                 .                  .
ATTGGGAACTTTGGGGAGGTGCGCCTCCTTGCCCCTCCTTGGCTGTGCCTCGGTGTCTCCTGGTTG
 I  G  N  F  G  E  V  R  L  P  L  L  G  C  L  G  V  S  W  L 740               760                780
          .                 .                  .
GTCGTCTTCCTCTGCCTCATCCGAGGGGTCAAGTCTTCAGGGAAAGTGGTGTACTTCACG
 V  V  F  L  C  L  I  R  G  V  K  S  S  G  K  V  V  Y  F  T 800               820                840
          .                 .                  .
GCCACGTTCCCCTACGTGGTGCTGACCATTCTGTTTGTCCGCGGAGTGACCCTGGAGGGA
 A  T  F  P  Y  V  V  L  T  I  L  F  V  R  G  V  T  L  E  G
```

FIGURE 7D

```
       860                880                900
        .                  .                  .
GCCTTTGACGGGCATCATGTACTACCTAACCCCGCAGTGGGACAAGATCCTGGAGGCCAAG
 A  F  D  G  I  M  Y  Y  L  T  P  Q  W  D  K  I  L  E  A  K

920
        .
GTGTGGGGTGATGCTGCCTCC
 V  W  G  D  A  A  S
```

DNA ENCODING A GLYCINE TRANSPORTER AND USES THEREOF

This application is a divisional of U.S. Ser. No. 08/240,783, filed Nov. 10, 1994, now U.S. Pat. No. 5,756,348 which is the National Stage filing of PCT/US92/09662, filed Nov. 12, 1992 which is a-continuation-in-part of U.S. Ser. No. 791,927, filed Nov. 12, 1991, now abandoned, the contents of which are incorporated by reference into the present disclosure.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

An essential property of synaptic transmission is the rapid termination of action following neurotransmitter release. For many neurotransmitters including catecholamines, serotonin, and certain amino acids (e.g., gamma-aminobutyric acid (GABA), glutamate, and glycine), rapid termination of synaptic action is achieved by the uptake of the transmitter into the presynaptic terminal and surrounding glial cells (Bennett et al., 1974; Horn, 1990; Kanner and Schuldiner, 1987). Inhibition or stimulation of neurotransmitter uptake provides a means for modulating the strength of the synaptic action by regulating the available levels of endogenous transmitters. The development of selective inhibitors may therefore represent a novel therapeutic approach to the treatment of neurological disorders.

The amino acid glycine is an important neurotransmitter in the vertebrate central nervous system, where it serves two distinct functions. First, glycine is a classical inhibitory neurotransmitter with a well established role in the spinal cord, brainstem, and retina (Aprison, 1990; Daly, 1990; Cortes and Palacios, 1990). The inhibitory effects of glycine are mediated by the glycine receptor, a ligand-gated chloride channel which is activated by glycine and competitively antagonized by strychnine (Grenningloh et al., 1987). Blockade of glycinergic transmission by strychnine causes seizures in animals and humans. Thus, agents which enhance the inhibitory role of glycine in the CNS may ameliorate the symptoms of epilepsy or other neurological disorders associated with excessive neural and/or musculoskeletal activity. This hypothesis is supported by the finding that defects in the glycine receptor underlie the hereditary myoclonus observed in certain mutant strains of mice (Becker, 1990) and calves (Gundlach, 1990).

In addition to its inhibitory role, glycine also modulates excitatory neurotransmission by potentiating the action of glutamate at NMDA receptors, both in hippocampus and elsewhere (Johnson and Ascher, 1987; for review, see Fletcher et al., 1990). The glycine regulatory site on the NMDA receptor is distinct from the strychnine-sensitive glycine receptor (Fletcher et al., 1990). The NMDA class of glutamate receptors is known to play a critical role in long-term potentiation, a cellular model of learning (Collingridge and Bliss, 1987). Recent evidence suggests that activation of the glycine regulatory site on the NMDA receptor may enhance cognitive function (Handelmann et al., 1989).

The molecular properties of glycine transport, particularly in relation to the dual role of glycine in the nervous system, have not previously been studied. Elucidation of the molecular structure of the synaptic glycine transporter is an important step in understanding glycinergic transmission and modulation. In particular, we were interested in exploring whether separate transporter mRNAs encode the uptake proteins that regulate inhibitory transmission and those that modulate glutamatergic transmission or whether one transporter mediates both functions.

SUMMARY OF THE INVENTION

This invention provides an isolated nucleic acid molecule encoding a mammalian glycine transporter. In one embodiment of this invention, the nucleic acid molecule comprises a plasmid designated pSVL-rB20a (ATCC Accession No. 75132, deposited Oct. 30, 1991). In the preferred embodiment this invention provides an isolated nucleic acid molecule encoding a human glycine transporter. In one embodiment of this invention, the nucleic acid molecule comprises a plasmid designated pBluescript-hTC27a (ATCC Accession No. 75342, deposited Nov. 6, 1992).

This invention provides a nucleic acid probe comprising a nucleic acid molecule of at least 15 nucleotides capable of specifically hybridizing with a sequence included within the sequence of a nucleic acid molecule encoding a mammalian glycine transporter. This invention also provides a nucleic acid probe comprising a nucleic acid molecule of at least 15 nucleotides capable of specifically hybridizing with a sequence included within the sequence of a nucleic acid molecule encoding a human glycine transporter.

This invention provides an antisense oligonucleotide having a sequence capable of binding specifically to an mRNA molecule encoding a mammalian glycine transporter so as to prevent translation of the mRNA molecule. This invention further provides an antisense oligonucleotide having a sequence capable of binding specifically to an mRNA molecule encoding a human glycine transporter so as to prevent translation of the mRNA molecule.

A monoclonal antibody directed to a mammalian glycine transporter is also provided by this invention. A monoclonal antibody directed to a human glycine transporter is further provided by this invention.

This invention provides a pharmaceutical composition comprising an amount of a substance effective to alleviate the abnormalities resulting from overexpression of a mammalian glycine transporter and a pharmaceutically acceptable carrier as well as a pharmaceutical composition comprising an amount of a substance effective to alleviate abnormalities resulting from underexpression of glycine transporter and a pharmaceutically acceptable carrier.

This invention further provides a pharmaceutical composition comprising an amount of a substance effective to alleviate the abnormalities resulting from overexpression of a mammalian glycine transporter and a pharmaceutically acceptable carrier as well as a pharmaceutical composition comprising an amount of a substance effective to alleviate abnormalities resulting from underexpression of glycine transporter and a pharmaceutically acceptable carrier.

This invention provides a transgenic, nonhuman mammal whose genome comprises DNA encoding a mammalian glycine transporter so placed positioned within such genome as to be transcribed into antisense mRNA complementary to mRNA encoding the glycine transporter and when hybridized to mRNA encoding the glycine transporter, the complementary mRNA reduces the translation of the mRNA encoding the glycine transporter.

This invention provides a transgenic, nonhuman mammal whose genome comprises DNA encoding a human glycine transporter so placed positioned within such genome as to be transcribed into antisense mRNA complementary to mRNA encoding the glycine transporter and when hybridized to mRNA encoding the glycine transporter, the complementary mRNA reduces the translation of the mRNA encoding the glycine transporter.

This invention also provides a transgenic, nonhuman mammal whose genome comprises DNA encoding a mammalian glycine transporter so placed positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention also provides a transgenic, nonhuman mammal whose genome comprises DNA encoding a human glycine transporter so placed positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention provides a method of screening drugs to identify drugs which specifically interact with, and bind to, a mammalian glycine transporter on the surface of a cell which comprises contacting a mammalian cell comprising an isolated DNA molecule encoding a mammalian glycine transporter, the protein encoded thereby is expressed on the cell surface, with a plurality of drugs, determining those drugs which bind to the mammalian cell, and thereby identifying drugs which specifically interact with, and bind to, a mammalian glycine transporter.

This invention provides a method of screening drugs to identify drugs which specifically interact with, and bind to, a human glycine transporter on the surface of a cell which comprises contacting a mammalian cell comprising an isolated DNA molecule encoding a human glycine transporter, the protein encoded thereby is expressed on the cell surface, with a plurality of drugs, determining those drugs which bind to the mammalian cell, and thereby identifying drugs which specifically interact with, and bind to, a human glycine transporter.

This invention also provides a method of determining the physiological effects of expressing varying levels of mammalian glycine transporters which comprises producing a transgenic nonhuman animal whose levels of mammalian glycine transporter expression are varied by use of an inducible promoter which regulates mammalian glycine transporter expression.

This invention also provides a method of determining the physiological effects of expressing varying levels of human glycine transporters which comprises producing a transgenic nonhuman animal whose levels of human glycine transporter expression are varied by use of an inducible promoter which regulates human glycine transporter expression.

This invention further provides a method of determining the physiological effects of expressing varying levels of mammalian glycine transporters which comprises producing a panel of transgenic nonhuman animals each expressing a different amount of mammalian glycine transporter.

This invention further provides a method of determining the physiological effects of expressing varying levels of human glycine transporters which comprises producing a panel of transgenic nonhuman animals each expressing a different amount of human glycine transporter.

This invention provides a method for diagnosing a predisposition to a disorder associated with the expression of a specific mammalian glycine transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a mammalian glycine transporter and labelled with a detectable marker; e.) detecting labelled bands which have hybridized to the DNA encoding a mammalian glycine transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for diagnosing a predisposition to a disorder associated with the expression of a specific human glycine transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a human glycine transporter and labelled with a detectable marker; e.) detecting labelled bands which have hybridized to the DNA encoding a human glycine transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for determining whether a substrate not known to be capable of binding to a mammalian glycine transporter can bind to the mammalian glycine transporter which comprises contacting a mammalian cell comprising an isolated DNA molecule encoding the mammalian glycine transporter with the substrate under conditions permitting binding of substrates known to bind to a transporter, detecting the presence of any of the substrate bound to the glycine transporter, and thereby determining whether the substrate binds to the mammalian glycine transporter.

This invention provides a method for determining whether a substrate not known to be capable of binding to a human glycine transporter can bind to the mammalian glycine transporter which comprises contacting a mammalian cell comprising an isolated DNA molecule encoding the human glycine transporter with the substrate under conditions permitting binding of substrates known to bind to a transporter, detecting the presence of any of the substrate bound to the glycine transporter, and thereby determining whether the substrate binds to the human glycine transporter.

BRIEF DESCRIPTION OF THE FIGURES

FIG. 2. Comparison of the rat glycine transporter with the human norepinephrine transporter (SEQ ID NO. 3) and the rat GABA transporter (SEQ ID NO. 4). The twelve putative α-helical membrane spanning domains (I–XII) are indicated by brackets. Identical residues are shaded. Glycine is the rat glycine transporter; Gaba is the rat GABA transporter (GAT-1); Norepi is the human norepinephrine transporter.

FIG. 3. Glycine transport by COS cells transfected with clone rB20a. Non-transfected COS cells (control) or COS cells transfected with rB20a were incubated for 10 minutes with 50 nM [$^3$H]glycine (sp. act.45Ci/mmole) in either HBS (containing 150 mM Nacl) or in a similar solution in which $Na^+$ was replaced by equimolar Li ($Na^+$-free), or $Cl^-$ was replaced by acetate (except for calcium chloride, which was replaced by calcium gluconate; $Cl^-$-free). Data show the specific uptake of glycine, expressed as cpm per mg cellular protein (mean±S. D. of triplicate determinations). Data are from a single experiment which was repeated with similar results.

Total RNA (30 μg/lane) isolated from various rat brain regions and peripheral tissues was separated on formaldehyde/agarose gels, blotted, and hybridized with $^{32}$P-labeled glycine transporter CDNA. The autoradiogram was developed after a six day exposure. Size standards are indicated at the left in kilobases. The hybridizing transcript is≈3.8 kb. RNA levels were normalized by reprobing the blot with a cDNA probe, designated p1B15, against cyclophilin. Similar results were obtained by using a probe to β-actin. Quantitation of the RNA blot was performed by densitometer scanning.

Figure 6A:
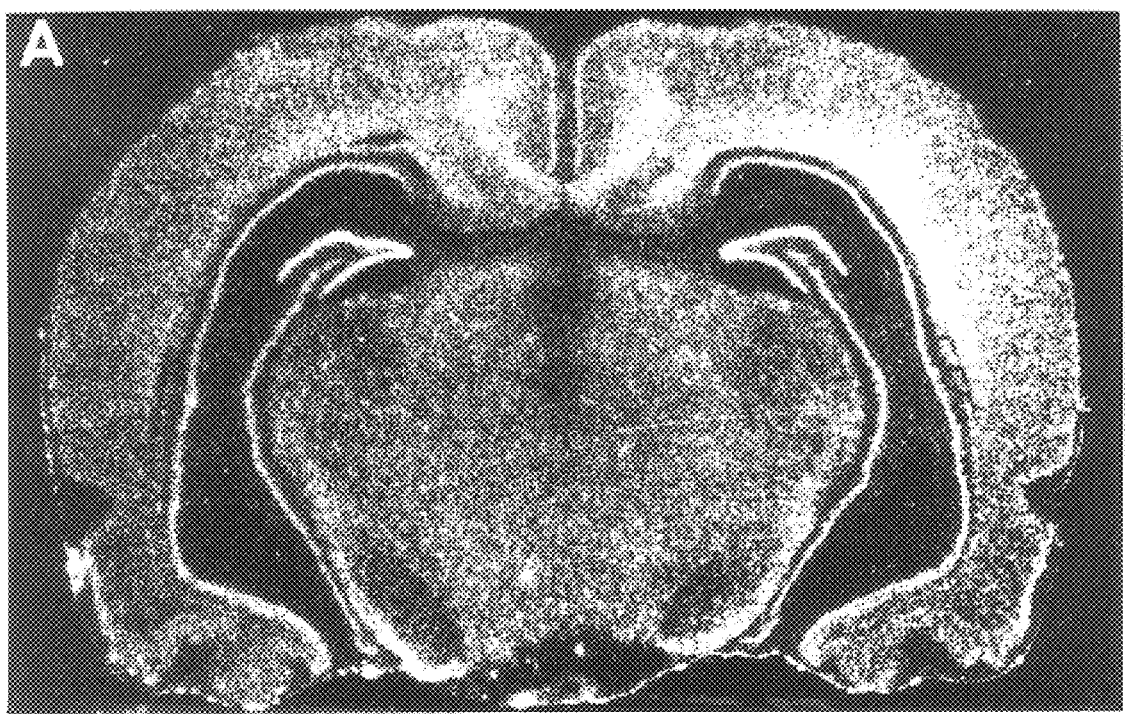
Figure 6B:
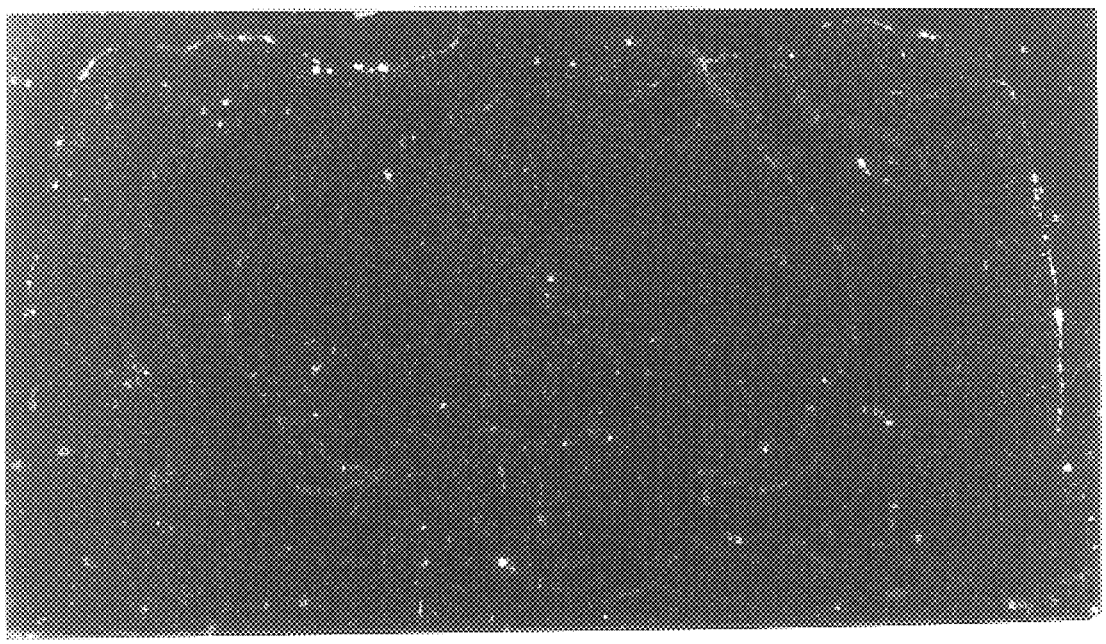

FIG. 6. In situ hybridization of glycine transporter mRNA in rat brain. A) Coronal sections of rat brain were hybridized with an $^{35}$S-labeled oligonucleotide probe complementary to the 3' untranslated region of the glycine transporter mRNA and exposed to X-OMAT film for 4 days. Note prominent labeling of the dentate gyrus and areas CA1, CA2, and CA3 of the hippocampal formation.

B) Parallel sections hybridized with the sense oligonucleotide showed insignificant labeling. No labeling was detected in sections pretreated with RNase A.

FIG. 7. Nucleotide Sequence (SEQ ID NO. 5) and Deduced Amino Acid Sequence (SEQ ID NO. 6) of the Human Glycine Transporter. Nucleotides are presented in the 5' to 3' orientation and the coding region is numbered starting from the putative initiating methionine. DNA sequence was determined by the chain termination method of Sanger (1977) on denatured double-stranded plasmid templates using Sequenase. Deduced amino acid sequence (single letter abbreviation) by translation of a long open reading frame is shown.

DETAILED DESCRIPTION OF THE INVENTION

This invention provides an isolated nucleic acid molecule encoding a mammalian glycine transporter. This invention further provides an isolated nucleic acid molecule encoding a human glycine transporter. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian glycine transporter and RNA, cDNA or genomic DNA encoding a human glycine transporter. As used herein, "glycine transporter" means a molecule which, under physiologic conditions, is substantially specific for the neurotransmitter glycine, is saturable, and of high affinity for glycine ($K_m≈100$ uM), and is time and ion dependent. One embodiment of this invention is an isolated nucleic acid molecule encoding a mammalian glycine transporter. Such a molecule may have coding sequences substantially the same as the coding sequence shown in FIG. 1. (Sequence I.D. No. 1). The DNA molecule of FIG. 1 encodes the sequence of the mammalian glycine transporter gene. Another, preferred embodiment is an isolated nucleic acid molecule encoding a human glycine transporter. Such a molecule may have coding sequences substantially the same as the coding sequence shown in FIG. 7. (Sequence I.D. Nos. 5 and 6). The DNA molecule of FIG. 7 (Sequence I.D. Nos. 5 and 6) encodes the sequence of the human glycine transporter gene. One means of isolating a mammalian glycine transporter is to probe a mammalian genomic DNA library with a natural or artificially designed DNA probe, using methods well known in the art. Another means of isolating a mammalian glycine transporter is to probe a mammalian cDNA library with natural or artificially designed DNA, using methods well known in the art. In the preferred embodiment of this invention, the mammalian glycine transporter is a human protein and the nucleic acid molecule encoding a human glycine transporter is isolated from a human cDNA library. In another embodiment of this invention the nucleic acid molcule encoding a human glycine transporter is isolated from a human genomic DNA library. DNA probes derived from the rat glycine transporter gene rB20a are useful probes for this purpose. DNA and cDNA molecules which encode mammalian glycine transporters are used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides an isolated nucleic acid molecule which has a nucleic acid sequence which differs from the sequence of a nucleic acid molecule encoding a glycine transporter at one or more nucleotides and which does not encode a protein having glycine transporter activity. As used herein "glycine transporter activity" means the ability of the protein to transport glycine. An example of such nucleic acid molecule is an isolated nucleic acid molecule which has an in-frame stop codon inserted into the coding sequence such that the transcribed RNA is not translated into protein.

Figure 1H:
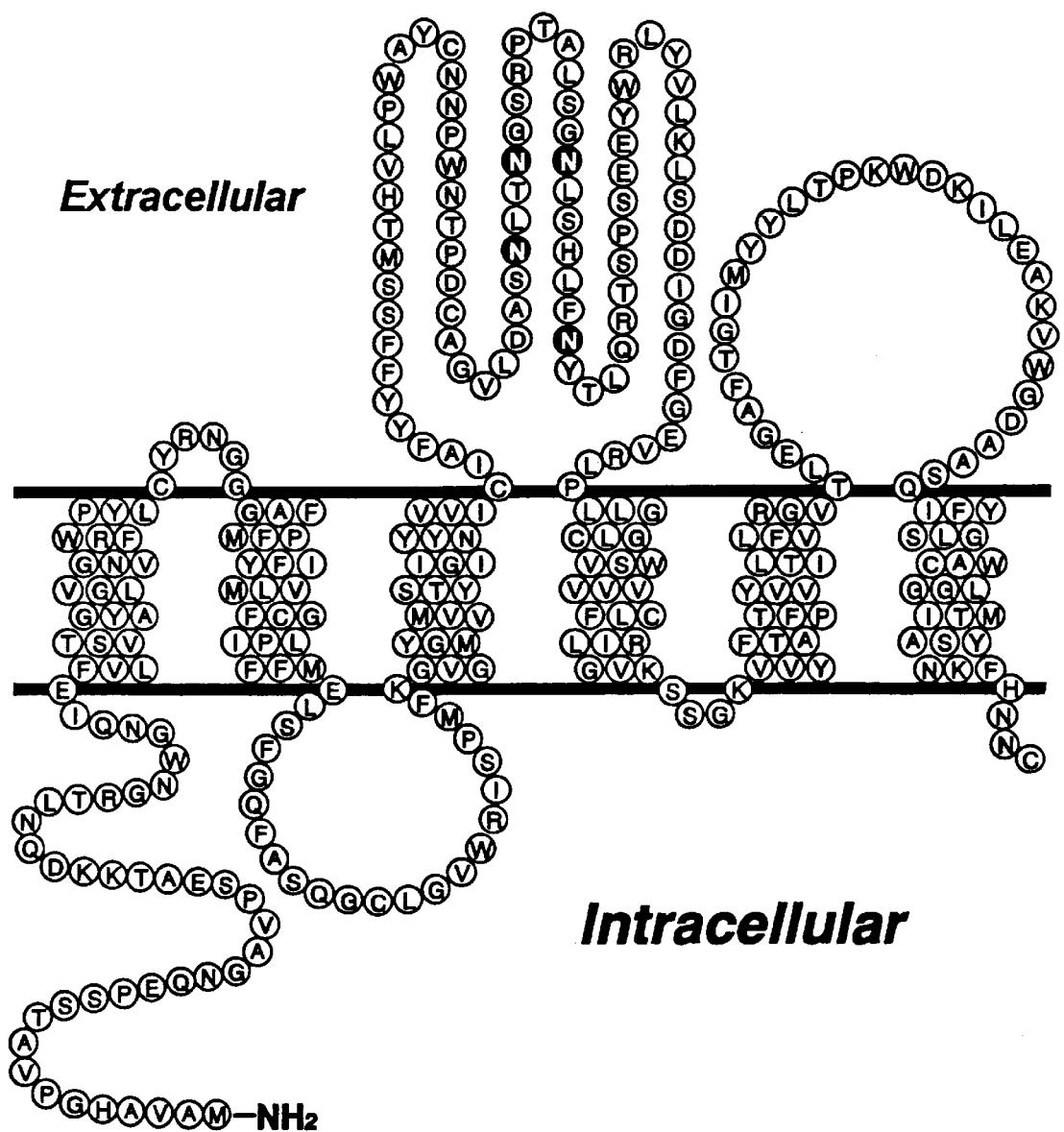
FIG. 1. Nucleotide Sequence (SEQ ID NO. 1), Deduced Amino Acid Sequence (SEQ ID NO. 2) and Putative Membrane Topology of the Rat Glycine Transporter. (A). Nucleotides are presented in the 5' to 3' orientation and the coding region is numbered starting from the putative initiating methionine and ending in the termination codon. DNA sequence was determined by the chain termination method of Sanger (1977) on denatured double-stranded plasmid templates using Sequenase. (B). Deduced amino acid sequence (designated by single letter abbreviation) by translation of a long open reading frame is shown. The transporter has been modeled with a similar topology to the previously cloned GABA transporter GAT-1 (Guastella et al., 1990). Postulated N-linked glycosylation sites are shaded.
Figure 1I:
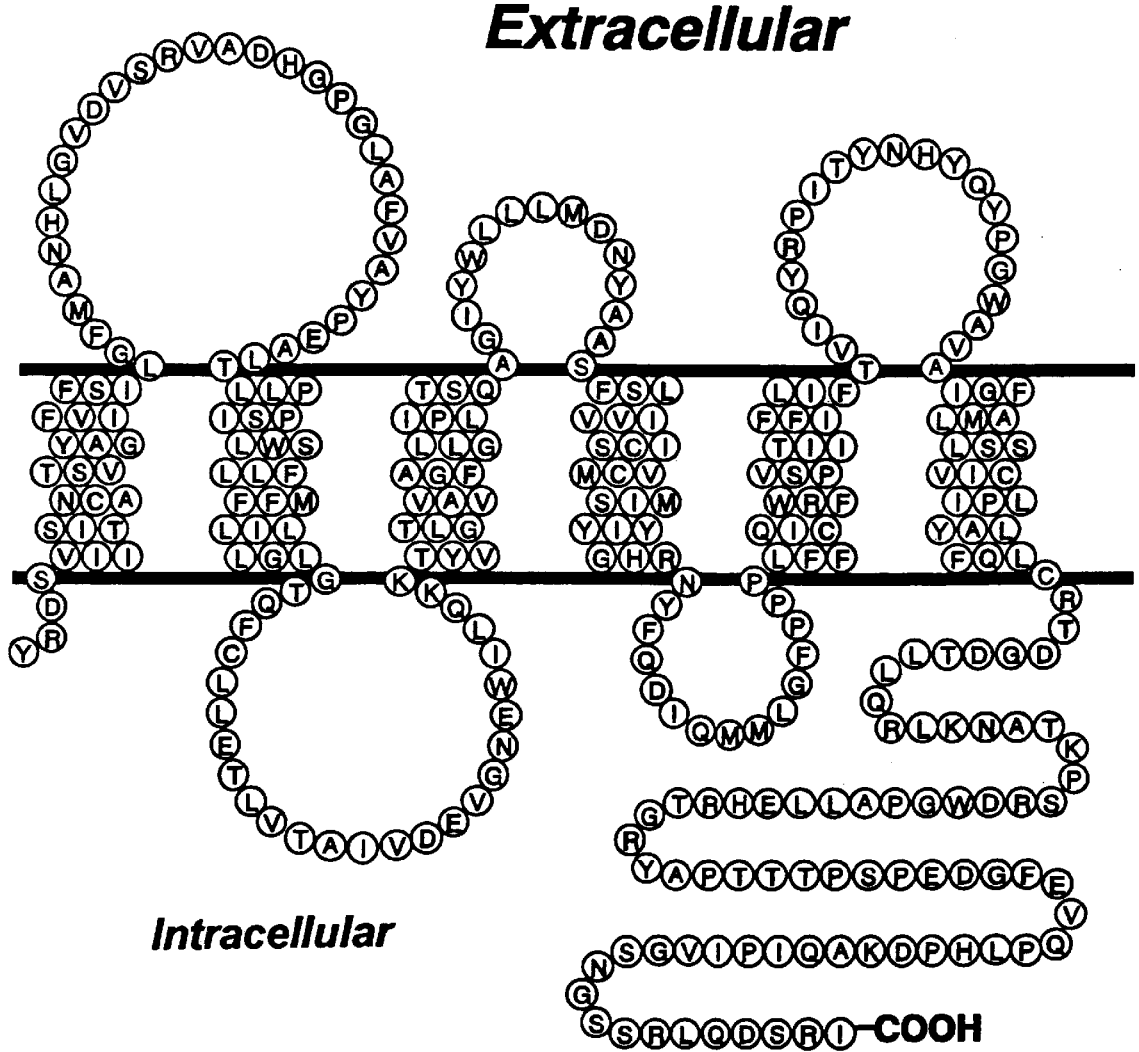

This invention provides a cDNA molecule encoding a mammalian glycine transporter, wherein the cDNA molecule has a coding sequence substantially the same as the coding sequence shown in FIG. 1. (Sequence I.D. No. 1). This invention further provides a cDNA molecule encoding a human glycine transporter, wherein the cDNA molecule has a coding sequence substantially the same as the coding sequence shown in FIG. 7. (Sequence I.D. Nos. 5 and 6). These molecules and their equivalents were obtained by the means described above.

This invention also provides an isolated protein which is a mammalian glycine transporter. In one embodiment of this invention, the protein is a mammalian glycine transporter protein having an amino acid sequence substantially similar to the amino acid sequence shown in FIG. 1 (Sequence I.D. Nos. 1 and 2). In the preferred embodiment of this invention, the protein is a human glycine transporter protein having an amino acid sequence substantially similar to the amino acid sequence shown in FIG. 7. (Sequence I.D. Nos. 5 and 6). As used herein, the term "isolated protein" is intended to encompass a protein molecule free of other cellular components. One means for obtaining isolated glycine transporter is to express DNA encoding the transporter in a suitable host, such as a bacterial, yeast, or mammalian cell, using methods well known to those skilled in the art, and recovering the transporter protein after it has been expressed in such a host, again using methods well known in the art. The transporter may also be isolated from cells which express it, in particular from cells which have been transfected with the expression vectors described below in more detail.

This invention also provides a vector comprising an isolated nucleic acid molecule such as DNA, RNA, or cDNA, encoding a mammalian glycine transporter. This invention also provides a vector comprising an isolated nucleic acid molecule such as DNA, RNA, or cDNA, encoding a human glycine transporter. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. A specific example of such plasmid is a plasmid comprising cDNA having a coding sequence substantially the same as the coding sequence shown in FIG. 1 and designated clone pSVL-rB20a and deposited under ATCC Accession No. 75132. Another example of such plasmid is a plasmid comprising cDNA encoding a human glycine transporter having a coding sequence substantially the same as the coding sequence shown in FIG. 7. Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a mammalian glycine transporter, adapted for expression in a bacterial cell, a yeast cell, or a mammalian cell which additionally comprise the regulatory elements necessary for expression of the DNA in the bacterial, yeast, or mammalian cells so located relative to the DNA encoding a mammalian glycine transporter as to permit expression thereof. DNA having coding sequences substantially the same as the coding sequence shown in FIG. 1 may usefully be inserted into the vectors to express mammalian glycine transporters. This invention also provides vectors comprising a DNA molecule encoding a human glycine transporter, adapted for expression in a bacterial cell, a yeast cell, or a mammalian cell which additionally comprise the regulatory elements necessary for expression of the DNA in the bacterial, yeast, or mammalian cells so located relative to the DNA encoding a human glycine transporter as to permit expression thereof. DNA having coding sequences substantially the same as the coding sequence shown in FIG. 7 may usefully be inserted into the vectors to express human glycine transporters. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the transporter. Certain uses for such cells are described in more detail below.

In one embodiment of this invention a plasmid is adapted for expression in a bacterial, yeast, or, in particular, a mammalian cell wherein the plasmid comprises a DNA molecule encoding a mammalian glycine transporter and the regulatory elements necessary for expression of the DNA in the bacterial, yeast, or mammalian cell so located relative to the DNA encoding a mammalian glycine transporter as to permit expression thereof. In another embodiment of this invention a plasmid is adapted for expression in a bacterial, yeast, or, in particular, a mammalian cell wherein the plasmid comprises a DNA molecule encoding a human glycine transporter and the regulatory elements necessary for expression of the DNA in the bacterial, yeast, or mammalian cell so located relative to the DNA encoding a human glycine transporter as to permit expression thereof. Suitable plasmids may include, but are not limited to plasmids adapted for expression in a mammalian cell, e.g., pSVL, pcEXV-3. A specific example of such a plasmid adapted for expression in a mammalian cell is a plasmid comprising cDNA having coding sequences substantially the same as the coding sequence shown in FIG. 1 and the regulatory elements necessary for expression of the DNA in the mammalian cell. This plasmid has been designated pSVL-rB20a and deposited under ATCC Accession No. 75132. A preferred embodiment of such a plasmid adapted for expression in a mammalian cell is a plasmid comprising cDNA encoding a human glycine transporter having coding sequences substantially the same as the coding sequence shown in FIG. 7 and the regulatory elements necessary for expression of the DNA in the mammalian cell. This plasmid has been designated pBluescript-hTC27a and deposited under ATCC Accession No. 75342, deposited Nov. 6, 1992.

Those skilled in the art will readily appreciate that numerous plasmids adapted for expression in a mammalian cell which comprise DNA encoding mammalian glycine transporters or a human glycine transporters and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra was made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a mammalian glycine transporter, such as a mammalian cell comprising a plasmid adapted for expression in a mammalian cell, which comprises a DNA molecule encoding a mammalian glycine transporter and the regulatory elements necessary for expression of the DNA in the mammalian cell so located relative to the DNA encoding a mammalian glycine transporter as to permit expression thereof. This invention provides a mammalian cell comprising a DNA molecule encoding a human glycine transporter, such as a mammalian cell comprising a plasmid adapted for expression in a mammalian cell, which comprises a DNA molecule encoding a human glycine transporter and the regulatory elements necessary for expression of the DNA in the mammalian cell so located relative to the DNA encoding a human glycine transporter as to permit expression thereof. Numerous mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, or DNA encoding these glycine transporters may be otherwise introduced into mammalian cells, e.g., by microinjection or electroporation, to obtain mammalian cells which comprise DNA, e.g., cDNA or a plasmid, encoding a mammalian glycine transporter or a human glycine transporter.

This invention provides a nucleic acid probe comprising a nucleic acid molecule of at least 15 nucleotides capable of specifically hybridizing with a sequence included within the sequence of a nucleic acid molecule encoding a mammalian glycine transporter, for example with a coding sequence included within the sequence shown in FIG. 1. This invention further provides a nucleic acid probe comprising a nucleic acid molecule of at least 15 nucleotides capable of specifically hybridizing with a sequence included within the sequence of a nucleic acid molecule encoding a human glycine transporter, for example with a coding sequence included within the sequence shown in FIG. 7. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding mammalian or human glycine transporters is useful as a diagnostic test for any disease process in which levels of expression of the corresponding glycine transporter are altered. DNA probe molecules are produced by insertion of a DNA molecule which encodes a mammalian or human glycine transporter or fragments thereof into suitable vectors, such as plasmids or bacteriophages, followed by insertion into suitable bacterial host cells and replication and harvesting of the DNA probes, all using methods well known in the art. For .example, the DNA may be extracted from a cell lysate using phenol and ethanol, digested with restriction enzymes corresponding to the insertion sites of the DNA into the vector (discussed above), electrophoresed, and cut out of the resulting gel. An example of such a DNA molecule is shown in FIG. 1 and FIG. 7. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian or a human transporter are useful as probes for these genes, for their associated mRNA, or for the isolation of related genes by homology screening of genomic or cDNA libraries, or by the use of amplification techniques such as the Polymerase Chain Reaction.

This invention also provides a method of detecting expression of a glycine transporter on the surface of a cell by detecting the presence of mRNA coding for a glycine transporter. This method comprises obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the glycine transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis, T. et al., Molecular Cloning; Cold Spring Harbor Laboratory, pp.197–98 (1982)). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a mammalian glycine transporter so as to prevent translation to the mammalian glycine transporter. The antisense oligonucleotide may have a sequence capable of binding specifically with any sequences of the cDNA molecule whose sequence is shown in FIG. 1. This invention further provides an antisense oligonucleotide having a sequence capable of binding specifically with any sequences of an mRNA molecule which encodes a human glycine transporter so as to prevent translation to the human glycine transporter. The antisense oligonucleotide may have a sequence capable of binding specifically with any sequences of the cDNA molecule whose sequence is shown in FIG. 7. As used herein, the phrase "binding specifically" means the ability of an antisense oligonucleotide to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a mammalian glycine transporter by passing through a cell membrane and binding specifically with mRNA encoding a mammalian glycine transporter in the cell so as to prevent its translation and a pharmaceutically acceptable hydrophobic carrier capable of passing through a cell membrane. DNA molecules having coding sequences substantially the same as the coding sequence shown in FIG. 1 may be used as the oligonucleotides of the pharmaceutical composition. This invention also provides a pharmaceutical composition comprising an effective amount of the oligonucleotide described above effective to reduce expression of a human glycine transporter by passing through a cell membrane and binding specifically with mRNA encoding a human glycine transporter in the cell so as to prevent its translation and a pharmaceutically acceptable hydrophobic carrier capable of passing through a cell membrane. DNA molecules having coding sequences substantially the same as the coding sequence shown in FIG. 7 may be used as the oligonucleotides of the pharmaceutical composition. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells.

This invention also provides a method of treating abnormalities which are alleviated by reduction of expression of a glycine transporter. This method comprises administering to a subject an effective amount of the pharmaceutical composition described above effective to reduce expression of the glycine transporter by the subject. This invention further provides a method of treating an abnormal condition related to glycine transporter activity which comprises administering to a subject an amount of the pharmaceutical composition described above effective to reduce expression of the glycine transporter by the subject. Several examples of such abnormal conditions are epilepsy, myoclonus, spastic paralysis, muscle spasm, schizophrenia, and cognitive impairment.

Antisense oligonucleotide drugs inhibit translation of mRNA encoding these transporters. Synthetic antisense oligonucleotides, or other antisense chemical structures are designed to bind to mRNA encoding the glycine transporter and inhibit translation of mRNA and are useful as drugs to inhibit expression of glycine transporter genes in patients. This invention provides a means to therapeutically alter levels of expression of mammalian glycine transporters by the use of a synthetic antisense oligonucleotide drug (SAOD) which inhibits translation of mRNA encoding these transporters. Synthetic antisense oligonucleotides, or other antisense chemical structures designed to recognize and selectively bind to mRNA, are constructed to be complementary to portions of the nucleotide sequences shown in FIG. 1 of DNA, RNA or of chemically modified, artificial nucleic acids. This invention further provides a means to therapeutically alter levels of expression of human glycine transporters by the use of a synthetic antisense oligonucleotide drug (SAOD) which inhibits translation of mRNA encoding these transporters. Synthetic antisense oligonucleotides, or other antisense chemical structures designed to recognize and selectively bind to mRNA, are constructed to be complementary to portions of the nucleotide sequences shown in FIG. 7 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequence shown in FIG. 1 or FIG. 7 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce transporter expression in particular target cells of a patient, in any clinical condition which may benefit from reduced expression of glycine transporters.

This invention provides an antibody directed to the mammalian glycine transporter. This antibody may comprise, for example, a monoclonal antibody directed to an epitope of a mammalian glycine transporter present on the surface of a cell, the epitope having an amino acid sequence substantially the same as an amino acid sequence for a cell surface epitope of the mammalian glycine transporter included in the amino acid sequence shown in FIG. 1. This invention further provides an antibody directed to the human glycine transporter. This antibody may comprise, for example, a monoclonal antibody directed to an epitope of a human glycine transporter present on the surface of a cell, the epitope having an amino acid sequence substantially the same as an amino acid sequence for a cell surface epitope of the human glycine transporter included in the amino acid sequence shown in FIG. 7. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 1 will bind to a surface epitope of a mammalian glycine transporter as described. Antibodies to the hydrophilic amino acid sequences shown in FIG. 7 will bind to a surface epitope of a human glycine transporter as described. Antibodies directed to the mammalian or human glycine transporters may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk$^-$ cells may be used as immunogens to raise such an antibody. Alternatively, synthetic peptides may be prepared using commercially available machines and the amino acid sequences shown in FIG. 1 and FIG. 7. As a still further alternative, DNA, such as a cDNA or a fragment thereof, may be cloned and expressed and the resulting polypeptide recovered and used as an immunogen. These antibodies are useful to detect the presence of mammalian glycine transporters encoded by the isolated DNA, or to inhibit the function of the transporters in living animals, in humans, or in biological tissues or fluids isolated from animals or humans.

This invention also provides a pharmaceutical composition which comprises an effective amount of an antibody directed to an epitope of the mammalian glycine transporter, effective to block binding of naturally occurring substrates to the glycine transporter, and a pharmaceutically acceptable carrier. A monoclonal antibody directed to an epitope of a mammalian glycine transporter present on the surface of a cell which has an amino acid sequence substantially the same as an amino acid sequence for a cell surface epitope of the mammalian glycine transporter included in the amino acid sequence shown in FIG. 1 is useful for this purpose.

This invention further provides a pharmaceutical composition which comprises an effective amount of an antibody directed to an epitope of a glycine transporter, effective to block binding of naturally occurring substrates to the glycine transporter, and a pharmaceutically acceptable carrier. A monoclonal antibody directed to an epitope of a mammalian glycine transporter present on the surface of a cell which has an amino acid sequence substantially the same as an amino acid sequence for a cell surface epitope of the mammalian glycine transporter included in the amino acid sequence shown in FIG. 1 is useful for this purpose.

This invention also provides a method of treating abnormalities in a subject which are alleviated by reduction of expression of a mammalian glycine transporter which comprises administering to the subject an effective amount of the pharmaceutical composition described above effective to block binding of naturally occurring substrates to the glycine transporter and thereby alleviate abnormalities resulting from overexpression of a mammalian glycine transporter. Binding of the antibody to the transporter prevents the transporter from functioning, thereby neutralizing the effects of overexpression. The monoclonal antibodies described above are both useful for this purpose.

This invention further provides a method of treating abnormalities in a subject which are alleviated by reduction of expression of a human glycine transporter which comprises administering to the subject an effective amount of the pharmaceutical composition described above effective to block binding of naturally occurring substrates to the glycine transporter and thereby alleviate abnormalities resulting from overexpression of a human glycine transporter. Binding of the antibody to the transporter prevents the transporter from functioning, thereby neutralizing the effects of overexpression. The monoclonal antibodies described above are both useful for this purpose.

This invention additionally provides a method of treating an abnormal condition related to an excess of glycine transporter activity which comprises administering to a subject an amount of the pharmaceutical composition described above effective to block binding of naturally occurring substrates to the glycine transporter and thereby alleviate the abnormal condition. Some examples of abnormal conditions are epilepsy, myoclonus, spastic paralysis, muscle spasm, schizophrenia, and cognitive impairment.

This invention provides a method of detecting the presence of a glycine transporter on the surface of a cell which comprises contacting the cell with an antibody directed to the mammalian glycine transporter, under conditions permitting binding of the antibody to the transporter, detecting the presence of the antibody bound to the cell, and thereby the presence of the mammalian glycine transporter on the surface of the cell. This invention further provides a method of detecting the presence of a glycine transporter on the surface of a cell which comprises contacting the cell with an antibody directed to the human glycine transporter, under conditions permitting binding of the antibody to the transporter, detecting the presence of the antibody bound to the cell, and thereby the presence of the human glycine transporter on the surface of the cell. Such a method is useful for determining whether a given cell is defective in expression of glycine transporters on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a mammalian glycine transporter. This invention also provides a transgenic nonhuman mammal expressing DNA encoding a human glycine transporter. This invention also provides a transgenic nonhuman mammal expressing DNA encoding a mammalian glycine transporter which has a nucleic acid sequence which differs from the sequence of a nucleic acid molecule encoding a glycine transporter at one or more nucleotides and which does not encode a protein having glycine transporter activity. This invention further provides a transgenic nonhuman mammal expressing DNA encoding a human glycine transporter which has a nucleic acid sequence which differs from the sequence of a nucleic acid molecule encoding a glycine transporter at one or more nucleotides and which does not encode a protein having glycine transporter activity.

This invention also provides a transgenic nonhuman mammal whose genome comprises DNA encoding a mammalian glycine transporter so placed as to be transcribed into antisense mRNA which is complementary to mRNA encoding a glycine transporter and which hybridizes to mRNA encoding a glycine transporter thereby reducing its translation. This invention further provides a transgenic nonhuman mammal whose genome comprises DNA encoding a human glycine transporter so placed as to be transcribed into antisense mRNA which is complementary to mRNA encoding a glycine transporter and which hybridizes to mRNA encoding a glycine transporter thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIG. 1 and FIG. 7. An example of a transgenic animal is a transgenic mouse. Examples of tissue specificity-determining regions are the metallothionein promoter (Low, M. J., Lechan, R. M., Hammer, R. E. et al. $_{Science}$ 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of mammalian glycine transporters or human glycine transporters are produced by creating transgenic animals in which the expression of a glycine transporter is either increased or decreased, or the amino acid sequence of the expressed glycine transporter protein is altered, by a variety of techniques. Examples of these techniques include, but are not limited to: 1) Insertion of normal or mutant versions of DNA encoding a mammalian glycine transporter or the human glycine transporter or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)) or, 2) Homologous recombination (Capecchi M. R. Science 244:1288–1292 (1989); Zimmer, A. and Gruss, P. Nature 15 338:150–153 (1989)) of mutant or normal, human or animal versions of these genes with the native gene locus in transgenic animals to alter the regulation of expression or the structure of these glycine transporters. The technique of homologous recombination is well known in the art. It replaces the native gene with the inserted gene and so is useful for producing an animal that cannot express native transporter but does express, for example, an inserted mutant transporter, which has replaced the native transporter in the animal's genome by recombination, resulting in underexpression of the transporter. Microinjection adds genes to the genome, but does not remove them, and so is useful for producing an animal which expresses its own and added transporters, resulting in overexpression of the transporter.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a mammalian glycine transporter is purified from a vector (such as plasmid pSVL-rB20a described above) by methods well known in the art. In the case of the human glycine transporter DNA or cDNA is purified from a vector pBluescript-hTC27a by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of transporter-specific drugs is to activate or to inhibit the transporter, the transgenic animal model systems described above are useful for testing the biological activity of drugs directed against these glycine transporters even before such drugs become available. These animal model systems are useful for predicting or evaluating possible therapeutic applications of drugs which activate or inhibit these glycine transporters by inducing or inhibiting expression of the native or trans-gene and thus increasing or decreasing expression of normal or mutant glycine transporters in the living animal. Thus, a model system is produced in which the biological activity of drugs directed against these glycine transporters are evaluated before such drugs become available. The transgenic animals which over or under produce the glycine transporter indicate by their physiological state whether over or under production of the glycine transporter is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less transporter by the affected cells, leading eventually to underexpression. Therefore, an animal which underexpresses transporter is useful as a test system to investigate whether the actions of such drugs which result in under expression are in fact therapeutic. Another use is that if overexpression is found to lead to abnormalities, then a drug which down-regulates or acts as an antagonist to the glycine transporter is indicated as worth developing, and if a promising therapeutic application is uncovered by these animal model systems, activation or inhibition of the glycine transporter is achieved therapeutically either by producing agonist or antagonist drugs directed against these glycine transporters or by any method which increases or decreases the expression of these glycine transporters in man.

Further provided by this invention is a method of determining the physiological effects of expressing varying levels of mammalian glycine transporters which comprises producing a transgenic nonhuman animal whose levels of mammalian glycine transporter expression are varied by use of an inducible promoter which regulates mammalian glycine transporter expression. This invention provides a method of determining the physiological effects of expressing varying levels of human glycine transporters which comprises producing a transgenic nonhuman animal whose levels of human glycine transporter expression are -varied by use of an inducible promoter which regulates mammalian glycine transporter expression. This invention also provides a method of determining the physiological effects of expressing varying levels of mammalian glycine transporters which comprises producing a panel of transgenic nonhuman animals each expressing a different amount of mammalian glycine transporter. This invention further provides a method of determining the physiological effects of expressing varying levels of human glycine transporters which comprises producing a panel of transgenic nonhuman animals each expressing a different amount of human glycine transporter. Such animals may be produced by introducing different amounts of DNA encoding a mammalian or human glycine transporter into the oocytes from which the transgenic animals are developed.

This invention also provides a method for identifying a substance capable of alleviating abnormalities resulting from overexpression of a mammalian or human glycine transporter comprising administering the substance to a transgenic nonhuman mammal expressing at least one artificially introduced DNA molecule encoding a mammalian or human glycine transporter and determining whether the substance alleviates the physical and behavioral abnormalities displayed by the transgenic nonhuman mammal as a result of overexpression of a mammalian or human glycine transporter. As used herein, the term "substance" means a compound or composition which may be natural, synthetic, or a product derived from screening. Examples of DNA molecules are DNA or cDNA molecules encoding a mammalian transporter encoding a mammalian glycine transporter having a coding sequence substantially the same as the coding sequence shown in FIG. 1. Examples of DNA molecules are DNA or cDNA molecules encoding a mammalian transporter encoding a human glycine transporter having a coding sequence substantially the same as the coding sequence shown in FIG. 7.

This invention provides a pharmaceutical composition comprising an amount of the substance described supra effective to alleviate the abnormalities resulting from overexpression of mammalian or human glycine transporter and a pharmaceutically acceptable carrier.

This invention further provides a method for treating the abnormalities resulting from overexpression of a mammalian or human glycine transporter which comprises administering to a subject an amount of the pharmaceutical composition described above effective to alleviate the abnormalities resulting from overexpression of a mammalian or human glycine transporter.

This invention provides a method for identifying a substance capable of alleviating the abnormalities resulting from underexpression of a mammalian or human glycine transporter comprising administering the substance to the transgenic nonhuman mammal described above which expresses only nonfunctional mammalian or human glycine transporter and determining whether the substance alleviates the physical and behavioral abnormalities displayed by the transgenic nonhuman mammal as a result of underexpression of a mammalian or human glycine transporter.

This invention also provides a pharmaceutical composition comprising an amount of a substance effective to alleviate abnormalities resulting from underexpression of a mammalian or human glycine transporter and a pharmaceutically acceptable carrier.

This invention further provides a method for treating the abnormalities resulting from underexpression of a mammalian or human glycine transporter which comprises administering to a subject an amount of the pharmaceutical composition described above effective to alleviate the abnormalities resulting from underexpression of a mammalian or human glycine transporter.

This invention provides a method for diagnosing a predisposition to a disorder associated with the expression of a specific mammalian glycine transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a mammalian glycine transporter and labelled with a detectable marker; e) detecting labelled bands which have hybridized to the DNA encoding a mammalian glycine transporter labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific mammalian glycine transporter allele.

This invention provides a method for diagnosing a predisposition to a disorder associated with the expression of a specific human glycine transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human glycine transporter and labelled with a detectable marker; e) detecting labelled bands which have hybridized to the DNA encoding a human glycine transporter labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human glycine transporter allele.

This invention provides a method of preparing the isolated glycine transporter which comprises inducing cells to express glycine transporter, recovering the transporter from the resulting cells, and purifying the transporter so recovered. An example of an isolated glycine transporter is an isolated protein having substantially the same amino acid sequence as the amino acid sequence shown in FIG. 1 or FIG. 7. For example, cells can be induced to express transporters by exposure to substances such as hormones. The cells can then be homogenized and the transporter isolated from the homogenate using an affinity column comprising, for example, glycine or another substance which is known to bind to the transporter. The resulting fractions can then be purified by contacting them with an ion exchange column, and determining which fraction contains transporter activity or binds anti-transporter antibodies.

This invention provides a method of preparing the isolated glycine transporter which comprises inserting nucleic acid encoding glycine transporter in a suitable vector, inserting the resulting vector in a suitable host cell, recovering the transporter produced by the resulting cell, and purifying the transporter so recovered. An example of an isolated glycine transporter is an isolated protein having substantially the same amino acid sequence as the amino acid sequence shown in FIG. 1 or FIG. 7. This method for preparing glycine transporter uses recombinant DNA technology methods well known in the art. For example, isolated nucleic acid encoding glycine transporter is inserted in a suitable vector, such as an expression vector. A suitable host cell, such as a bacterial cell, or a eukaryotic cell such as a yeast cell, is transfected with the vector. Glycine transporter is isolated from the culture medium by affinity purification or by chromatography or by other methods well known in the art.

This invention provides a method for determining whether a substrate not known to be capable of binding to a mammalian glycine transporter can bind to a mammalian glycine transporter which comprises contacting a mammalian cell comprising a DNA molecule encoding a mammalian glycine transporter with the substrate under conditions permitting binding of substrates known to bind to the glycine transporter, detecting the presence of any of the substrate bound to the glycine transporter, and thereby determining whether the substrate binds to the glycine transporter. The DNA in the cell may have a coding sequence substantially the same as the coding sequence shown in FIG. 1 preferably, the mammalian cell is nonneuronal in origin. An example of a nonneuronal mammalian cell is a Cos7 cell. The preferred method for determining whether a substrate is capable of binding to the mammalian glycine transporter comprises contacting a transfected nonneuronal mammalian cell (i.e. a cell that does not naturally express any type of glycine transporter, thus will only express such a transporter if it is transfected into the cell) expressing a glycine transporter on its surface, or contacting a membrane preparation derived from such a transfected cell, with the substrate under conditions which are known to prevail, and thus to be associated with, vivo binding of the substrates to a glycine transporter, detecting the presence of any of the substrate being tested bound to the glycine transporter on the surface of the cell, and thereby determining whether the substrate binds to the glycine transporter. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of mammalian glycine transporters with substrates as described above. Transfection systems are useful as living cell cultures for competitive binding assays between known or candidate drugs and substrates which bind to the transporter and which are labeled by radioactive, spectroscopic or other reagents. Membrane preparations containing the transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of the mammalian glycine transporter. The transfection system is also useful for determining the affinity and efficacy of known drugs at the mammalian glycine transporter sites.

This invention provides a method for determining whether a compound not known to be capable of specifically binding to a mammalian glycine transporter can specifically bind to the mammalian glycine transporter, which comprises contacting a mammalian cell comprising a plasmid adapted for expression in a mammalian cell which plasmid further comprises a DNA which expresses a mammalian glycine transporter on the cell's surface with the compound under conditions permitting binding of ligands known to bind to a mammalian glycine transporter, detecting the presence of any compound bound to the mammalian glycine transporter, the presence of bound compound indicating that the compound is capable of specifically binding to the mammalian glycine transporter.

This invention provides a method for determining whether a compound not known to be capable of specifically binding to a human glycine transporter can specifically bind to the human glycine transporter, which comprises contacting a mammalian cell comprising a plasmid adapted for expression in a mammalian cell which plasmid further comprises a DNA which expresses a human glycine transporter on the cell's surface with the compound under conditions permitting binding of ligands known to bind to a human glycine transporter, detecting the presence of any compound bound to the human glycine transporter, the presence of bound compound indicating that the compound is capable of specifically binding to the human glycine transporter.

This invention also provides a method of screening drugs to identify drugs which specifically interact with, and bind to, a mammalian glycine transporter on the surface of a cell which comprises contacting a mammalian cell comprising a DNA molecule encoding the mammalian glycine transporter on the surface of a cell with a plurality of drugs, detecting those drugs which bind to the mammalian cell, and thereby identifying drugs which specifically interact with, and bind to, the mammalian glycine transporter. The DNA in the cell may have a coding sequence substantially the same as the coding sequence shown in FIG. 1. This invention further provides a method of screening drugs to identify drugs which specifically interact with, and bind to, a human glycine transporter on the surface of a cell which comprises contacting a mammalian cell comprising a DNA molecule encoding the human glycine transporter on the surface of a cell with a plurality of drugs, detecting those drugs which bind to the mammalian cell, and thereby identifying drugs which specifically interact with, and bind to, the human glycine transporter. The DNA in the cell may have a coding sequence substantially the same as the coding sequence shown in FIG. 7. Various methods of detection may be employed. The drugs may be "labeled" by association with a detectable marker substance (e.g., radiolabel or a nonisotopic label such as biotin). Preferably, the mammalian cell is nonneuronal in origin. An example of a nonneuronal mammalian cell is a Cos7 cell. Drug candidates are identified by choosing chemical compounds which bind with high affinity to the expressed glycine transporter protein in transfected cells, using radioligand binding methods well known in the art, examples of which are shown in the binding assays described herein. Drug candidates are also screened for selectivity by identifying compounds which bind with high affinity to one particular glycine transporter subtype but do not bind with high affinity to any other glycine transporter subtype or to any other known transporter site. Because selective, high affinity compounds interact primarily with the target glycine transporter site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

Applicants have identified individual transporter subtype proteins and have described methods for the identification of pharmacological compounds for therapeutic treatments. Pharmacological compounds which are directed against specific transporter subtypes provide effective new therapies with minimal side effects.

Elucidation of the molecular structure of the neural glycine transporter is an important step in the understanding of glycinergic neurotransmission. This disclosure reports the isolation, amino acid sequence, and functional expression of a cDNA clone from rat brain which encodes a glycine transporter. This disclosure further reports the isolation, amino acid sequence, and functional expression of a cDNA clone from human brain which encodes a glycine transporter. The identification of these transporters will play a pivotal role in elucidating the molecular mechanisms underlying glycinergic transmission and neural modulation and should also aid in the development of novel therapeutic agents.

A complementary DNA clone (designated rB20a) encoding a transporter for glycine has been isolated from rat brain, and its functional properties have been examined in mammalian cells. The nucleotide sequence of rB20a predicts a protein of 638 amino acids, with 12 highly hydrophobic regions compatible with membrane-spanning domains. When incubated with 50 nM [$^3$H]glycine, COS cells transiently transfected with rB20a accumulate 50-fold as much radioactivity as non-transfected control cells. The transporter encoded by rB20a displays high-affinity for glycine ($K_m \approx 100$ uM) and is dependent on external sodium and chloride. In addition complementary DNA clone (designated hTC27a) encoding a transporter for glycine has been isolated from human brain. Analysis of the glycine transporter structure and function provides a model for the development of drugs useful as cognitive enhancers, and for the treatment of epilepsy and other neurological disorders.

This invention identifies for the first time a new transporter protein, its amino acid sequence, and its mammalian gene and its human gene. The information and experimental tools provided by this discovery are useful to generate new therapeutic agents, and new therapeutic or diagnostic assays for this new transporter protein, its associated mRNA molecule or its associated genomic DNA. The information and experimental tools provided by this discovery will be useful to generate new therapeutic agents, and new therapeutic or diagnostic assays for this new transporter protein, its associated mRNA molecule, or its associated genomic DNA.

Specifically, this invention relates to the first isolation of a mammalian cDNA and genomic clone encoding a glycine transporter. A new mammalian gene for the transporter identified herein as rB20a has been identified and characterized, and a series of related cDNA and genomic clones have been isolated. In addition, the mammalian glycine transporter has been expressed in Cos7 cells by transfecting the cells with the plasmid pSVL-rB20a. The pharmacological properties of the protein encoded have been determined, and these properties classify this protein as a glycine transporter. Mammalian cell lines expressing this mammalian glycine transporter at the cell surface have been constructed, thus establishing the first well-defined, cultured cell lines with which to study this glycine transporter.

This invention further relates to the first isolation of a human cDNA and genomic clone encoding a glycine transporter. The new human gene for the human transporter identified herein as hTC27a has been identified and characterized.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

Materials and Methods

Cloning and sequencing of Rat Glycine Transporter: A rat brain cDNA library in the Lambda ZAP II vector (Stratagene, La Jolla, Calif.) was screened at low stringency using overlapping probes representing the coding region of the rat GABA transporter cDNA (Guastella et al., 1990). Exact primers were used to generate PCR products encoding the GABA transporter from randomly-primed rat brain cDNA. Three sets of primers were designed from nucleotide sequence of the rat GABA transporter cDNA (Guastella et al., 1990) such that three products represented the entire coding region. Primer set one was made as a sense oligonucleotide derived from nucleotides −125 to −109 and an antisense oligonucleotide derived from nucleotides 721–737 to generate a PCR product of 862 bp; primer set two was composed of sense and antisense oligonucleotides derived from nucleotides 613–629 and 1417–1433, respectively, to generate a PCR product of 821 bp; primer set three was composed of sense and antisense oligonucleotides derived from nucleotides 1318–1334 and 1860–1876, respectively, to generate a PCR product of 559 bp. The 559 bp PCR product was gel purified, subcloned, and sequenced to confirm its identity; the others were gel purified and used directly as probes. All three probes were labeled with $^{32}$p by the method of random priming (Feinberg and Vogelstein, 1983). Hybridization was performed at 40° C. in a solution containing 25% formamide, 10% dextran sulfate, 5×SSC (1×SSC is 0.15 M sodium chloride, 0.015 M sodium citrate), 1×Denhardt's (0.02% polyvinylpyrrolidone, 0.02% Ficoll, and 0.02% bovine serum albumin), and 100 μg/ml of sonicated salmon sperm DNA. The filters were washed at 40° C. in 0.1×SSC containing 0.1% sodium dodecyl sulfate (SDS) and exposed at −70° C. to Kodak XAR film in the presence of one intensifying screen. Lambda phage hybridizing to the probe were plaque purified and screened with the same probe mixture at high stringency to eliminate exact matches. Candidate clones were converted to phagemids by in vivo excision with f1 helper phage. Nucleotide sequences of double-stranded cDNAs in pBluescript were analyzed by the Sanger dideoxy nucleotide chain-termination method (Sanger, 1977) using Sequenase (U.S. Biochemical Corp., Cleveland, Ohio).

Expression: Two cDNA clones which collectively span the entire coding region of the glycine transporter gene, including 63 base pairs of 5' untranslated sequence and 189 base pairs of 3' untranslated sequence, were identified. These two clones were constructed into a full-length clone (designated rB20a) by ligation at their internal Nco I sites and then cloned into the eukaryotic expression vector pSVL (Pharmacia LKB Biotechnology, Piscataway, N.J.). Transient transfection of COS cells was carried out using DEAE-dextran with DMSO according to the method of Lopata et al. (1984) with minor modifications. COS cells were grown in six-well plates (37° C.,5%$CO_2$) in high glucose Dulbecco's modified Eagle medium supplemented with 10% bovine calf serum, 100 U/ml penicillin G, and 100 µg/ml streptomycin sulfate. Cells were routinely used two days after transfection for transport studies.

Transport Studies: To measure glycine transport, COS cells grown in 6-well plates (well diameter=35 mm) were washed 3× with HEPES-buffered saline (HBS, in mM: NaCl, 150; HEPES, 20; $CaCl_2$, 1; glucose, 10; KCl, 5; $MgCl_2$, 1; pH 7.4) and allowed to equilibrate in a 37° C. water bath. After 10 minutes the medium was removed and a solution containing [$^3$H]glycine (New England Nuclear, sp. activity =45Ci/mmole) and required drugs in HBS was added (1.5 ml/well). Plates were incubated at 37° C. for 10 or 20 minutes, then washed rapidly 3× with HBS. Cells were solubilized with 0.05% sodium deoxycholate/0.1N NaOH (1 ml/well), 0.5 ml aliquots were removed, neutralized with 1N HCl, and radioactivity was determined by scintillation counting. Protein was quantified in an aliquot of the solubilized cells with the Bradford Reagent (Biorad, Richmond, Calif.), according to the manufacturer's directions. Non-specific uptake was defined in parallel wells with 1 mM unlabeled glycine, and was subtracted from total uptake (no competitor) to yield specific uptake; all data represent specific uptake.

Northern Blot Analysis: Total cellular RNA was isolated from rat tissues using RNAzol (Cinna/Biotecx Laboratories Inc.; Houston, Tex.) as outlined by the manufacturer. Denatured RNA samples (~30 µg) were separated in a 1.2% agarose gel containing 3.3% formaldehyde. RNAs were transferred to nitrocellulose membranes (Schleicher and Schuell, Keene, N. H.) by overnight capillary blotting in 10×SSC. Northern blots were rinsed and then baked for 2 hours at 80° C. under vacuum. Prehybridization was for 1 hour at 65° C. in a solution containing 50% formamide, 2×SSC, 1× Denhardt's, 0.1% SDS, 20 mM sodium phosphate, and 10 mm EDTA. Blots were hybridized overnight at 42° C. with $^{32}$P-labeled DNA probes (randomly primed) in prehybridization mixture containing 125 µg/ml sonicated salmon sperm DNA. The blots were washed successively in 2×SSC/1% SDS and 0.1×SSC/1% SDS at 65° C., then exposed to Kodak XAR-5 film with one intensifying screen at −90° C. for up to one week.

In Situ Hybridization: Male Sprague-Dawley rats (Charles River) were decapitated and the brains rapidly frozen in isopentane. Sections were cut on a cryostat, thaw-mounted onto poly-L-lysine coated coverslips, and stored at −80° C. until use. Tissue was fixed in 4% paraformaldehyde, treated with 5mM dithiothreitol (DTT), acetylated (0.25% acetic anhydride in 0.1M triethanolamine), and dehydrated. Tissue was prehybridized (1 hour, 40° C.) in a solution containing 50% formamide, 4×SSC (0.6M NaCl/0.06M sodium citrate), 1× Denhardt's solution (0.2% polyvinylpyrrolidine, 0.2% Ficoll, 0.2% bovine serum albumin), 50 mM DTT, 500 µg/ml salmon sperm DNA, 500 µg/ml yeast tRNA, 10% dextran sulfate, then hybridized overnight with $^{35}$S-labeled anti-sense oligonucleotides (45 mers) in the same solution. After washing and dehydration, sections were apposed to Kodak X-OMAT AR film-for 4 days at −20° C. To verify the specificity of the hybridization signal, parallel tissues were pretreated with 100 µg/ml RNase A (37°, 30 minutes) prior to hybridization. Two different oligonucleotides designed to separate regions of the glycine transporter (loop region between transmembrane domains III and IV, 3' untranslated region) showed identical patterns of hybridization.

Use of PCR to Identify Human cDNA Libraries for Screening: For hGlycine, the sequences of the rat PCR primers were 5'-(ATGGCTGTGGCTCACGGACCTGTGG) (SEQ ID NO. 7) and 5'-(TGAAGACTTGACTCCTCGAATGAGGCAGAG) (SEQ ID NO. 8). PCR reactions were carried out in a buffer containing 20 mM Tris (pH 8.3), 50 mM KCl, 1.5 mM $MgCl_2$, 0.001% gelatin, 2 mM dNTP's, 1 µM each primer, Taq polymerase, and an aliquot of a lambda phage library, water, or a control plasmid for 40 cycles of 94° C. for 2 min., 50° C. for 2 min., and 72° C. for 3 min. PCR reactions were carried out as described above for 40 cycles of 94° C. for 2 min., 40° C. for 2 min., and 72° C. for 3 min. PCR products were separated by electrophoresis in 1.2% agarose gels, blotted to nylon membranes (Zeta-Probe GT; Bio-Rad Laboratories, Richmond, Calif.), and hybridized at 40° C. overnight with $^{32}$p-labeled oligonucleotide probes (overlapping 45mers) in a solution containing 25% formamide, 10% dextran sulfate, 5×SSC, 1× Denhardt's, and 100 µg/ml of sonicated salmon sperm DNA. The sequences of the oligonucleotides corresponded to amino acids 204–226 of the rat glycine transporter. Blots were washed at low stringency (0.1×SSC, 40° C.) and exposed to Kodak XAR film for up to three days with one intensifying screen at −70° C.

Isolation and sequencing of Human Clones: Human cDNA libraries in the Lambda ZAP or Lambda ZAP II vector (Stratagene, La Jolla, Calif.) that were identified as containing hGlycine were screened under reduced stringency (25% formamide, 40° C. hybridization; 0.1×SSC, 40° C. wash). Hybridizing lambda phage were plaque purified and converted to phagemids by in vivo excision with f1 helper phage. Nucleotide sequences of double-stranded cDNAs in pBluescript were analyzed by the Sanger dideoxy nucleotide chain-termination method (Sanger, 1977) using Sequenase (U.S. Biochemical Corp., Cleveland, Ohio).

Results

To clone the glycine transporter, a rat brain cDNA library was screened at low stringency with probes encoding the rat GABA transporter (Guastella et al., 1990). Of 48 clones isolated, ten were identified which hybridized at low but not at high stringency with the GABA transporter probes. DNA sequence analysis revealed that seven of these clones contained overlapping fragments. Two of the clones were identified which together comprised a 2.2 kb sequence (rB20a) with an open reading frame of 1917 base pairs. Comparison of this sequence with the rat GABA transporter revealed 55–60% nucleotide identity within the coding region. Searches of Genbank and EMBL data bases demonstrated that the nucleotide sequence was novel and that the two most closely related sequences were the rat GABA transporter (Guastella et al., 1990) and the human norepinephrine transporter (Pacholczyk et al., 1991).

Figure 2B:
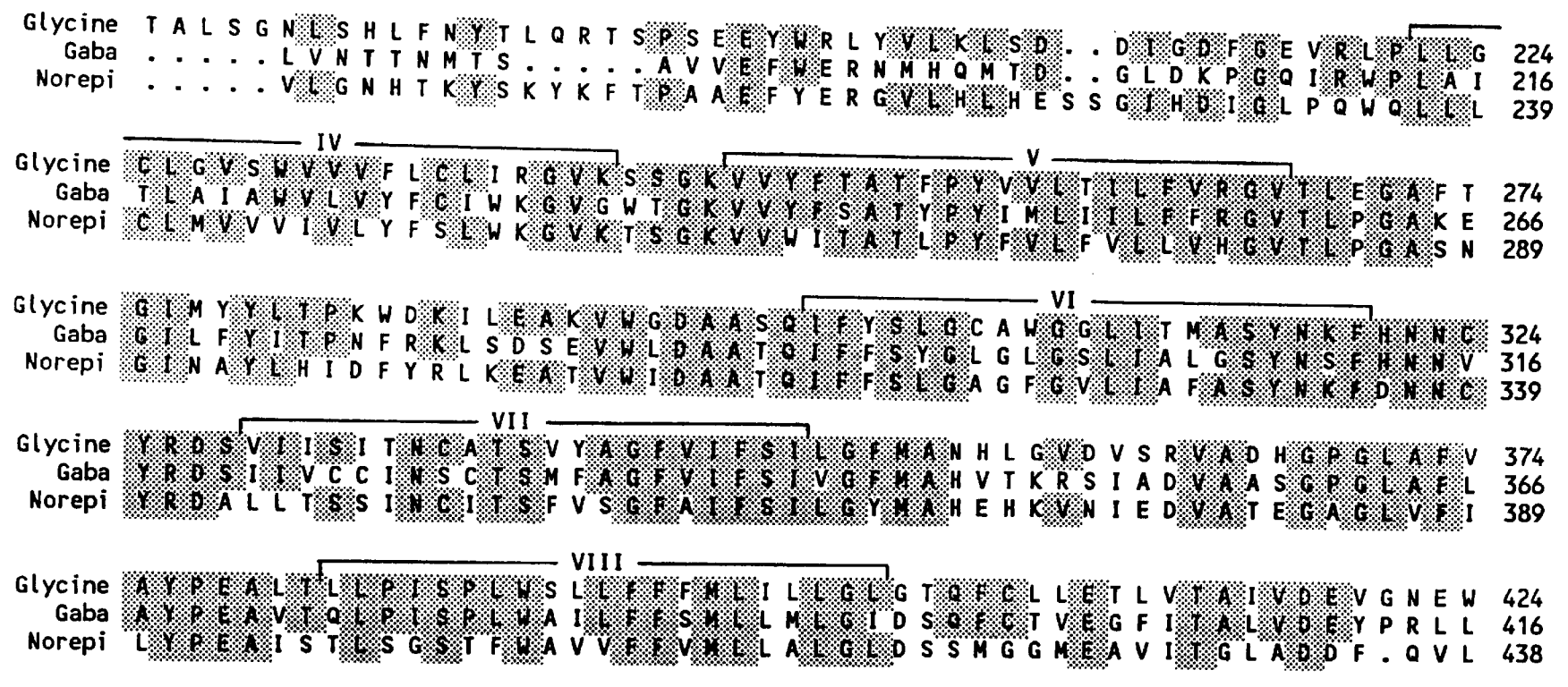

The nucleotide and deduced amino acid sequence and proposed membrane topology of the protein encoded by rB20a is shown in FIG. 1. An open reading frame extending from an ATG start codon at position 1 to a stop codon at position 1917 can encode a protein 638 amino acids in length, having a relative molecular mass ($M_r$) of approximately 72,000. Hydropathy analysis indicates the presence of 12 hydrophobic domains which may represent membrane spanning segments (data not shown). We have modeled the glycine transporter with both termini inside the cell, similar to the membrane topology proposed for the GABA (Guastella et al., 1990) and noradrenaline (Pacholczyk et al., 1991) transporters. Of six potential sites for Asn-linked glycosylation, four are found in the loop between the third and fourth transmembrane domains which is predicted to be extracellular. Alignment with the GABA transporter revealed 45% amino acid identity (68% homology with conservative substitutions). Comparison of rB20a with the human norepinephrine transporter (Pacholczyk et al., 1991) showed a similar degree of amino acid identity (42%) (FIG. 2). These data suggested that the new sequence encodes a novel transporter expressed in the brain. To explore this possibility, the sequence was placed in a mammalian expression vector (pSVL), transfected into COS cells, and screened for transport of a variety of radiolabeled neurotransmitters and amino acids.

COS cells transiently transfected with rB20a (COS/rB20a) accumulated more [$^3$H]glycine than non-transfected control cells (FIG. 3). During a 20 minute incubation (37° C.) with a low concentration of [$^3$H]glycine (50–100 nM), specific uptake was increased 54±6-fold over control (mean±SEM,n=6 experiments); a representative experiment is shown in FIG. 3. Specific uptake represented 45±4 and 87±1% (mean±SEM, n=6) of total uptake in control and transfected cells, respectively, and the absolute levels of non-specific uptake were similar in both cases. The high percentage of specific uptake observed in transfected cells demonstrates that the enhanced uptake resulting from expression of rB20a displays saturability. Uptake of [$^3$H] glycine was not increased following transfection with either a plasmid lacking the insert or containing an irrelevant insert (not shown), indicating that the enhanced uptake was specific for rB20a and was not due to non-specific perturbation of the membrane. Further, expression of rB20a did not significantly alter the uptake of [$^3$H]GABA, [$^3$H]histamine, [$^3$H]glutamate, [$^3$H]tyrosine, [$^3$H]norepinephrine, [$^3$H]5-HT, or [$^3$H]dopamine (data not shown). The transport of [$^3$H]glycine was decreased ≧95% when Na$^+$ was replaced by Li$^+$ (FIG. 3) or choline (not shown), or when Cl$^-$ was replaced by acetate and gluconate (FIG. 3). Thus, the glycine transporter encoded by rB20a displays an absolute requirement for Na$^+$ and Cl$^-$, similar to the cloned GABA transporter (Guastella et al., 1990). Taken together, these data indicate that rB20a encodes a saturable, sodium- and chloride-dependent glycine transporter.

Figure 4A:
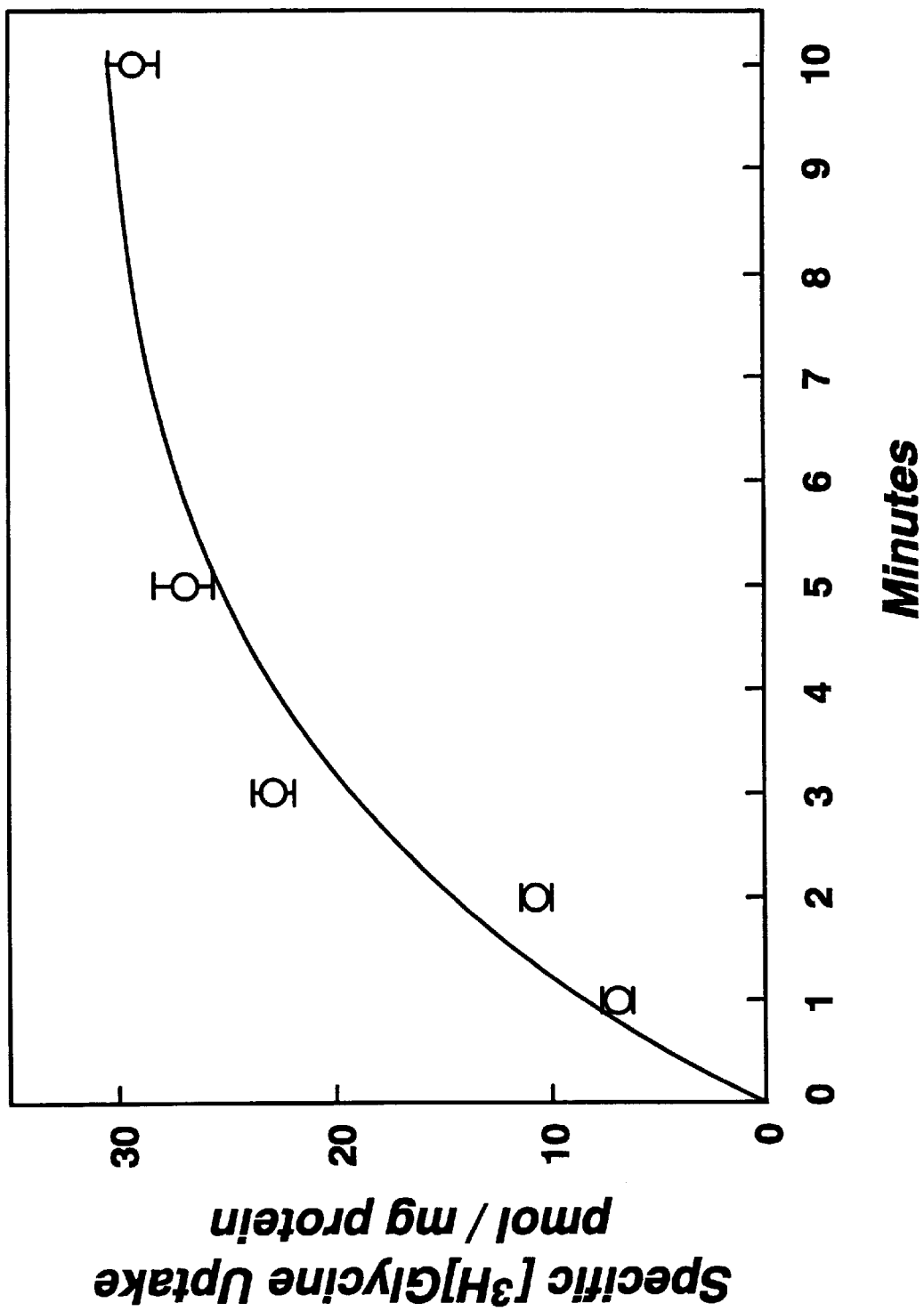
FIG. 4. Kinetic properties of the cloned glycine transporter. (A). Time-course of glycine transport. COS cells transfected with rB20a were incubated with 50 nM [$^3$H] glycine for the indicated times and the accumulated radioactivity was determined. Specific uptake is expressed as pmoles per mg cellular protein; data are from a single experiment that was repeated with similar results. (B). Concentration-dependence of glycine transport. COS cells transfected with rB20a cells were incubated with the indicated concentrations of [$^3$H]glycine for 30 seconds and the accumulated radioactivity was determined. The specific activity of the [$^3$H]glycine was reduced with unlabeled glycine. Data represent specific transport expressed as nmoles per mg cellular protein, and are from a single experiment that was repeated with similar results.

The kinetics of uptake of 50 nM [$^3$H]glycine in rB20a/COS cells are shown in FIG. 4A. The specific accumulation of [$^3$H]glycine was linear for the first few minutes and approached saturation by about 5 minutes. To determine the affinity of glycine for the cloned transporter, COS cells transfected with rB20a were incubated with various concentrations of [$^3$H]glycine and the specific accumulation of radioactivity was determined. A representative experiment is shown in FIG. 4B in which it can be seen that uptake saturated at higher concentrations of glycine, as expected for a carrier-mediated process. Non-linear regression analysis of the data indicate a $K_M$ of 123 μM and a $V_{MAX}$ of 28 nmoles per minute per mg protein (mean of 2 experiments).

To determine the pharmacological specificity of the transporter encoded by rB20a, we examined the ability of various agents to compete for the uptake of [$^3$H]glycine by COS cells transfected with rB20a (Table 1).

TABLE 1

Pharmacological Specificity of [$^3$H]glycine Uptake In COS-7 Cells Transfected with rB20a

| Inhibitor[a] | concentration | % displacement |
|---|---|---|
| L-alanine | 1 mM | 2 |
| dopamine | 1 mM | 0 |
| GABA | 1 mM | 0 |
| glycine | 1 mM | 100 |
| L-glutamate | 1 mM | 0 |
| glycine ethyl ester | 10 μM | 0 |
|  | 100 μM | 0 |
|  | 1 mM | 32 |
| glycine methyl ester | 10 μM | 0 |
|  | 100 μM | 0 |
|  | 1 mM | 42 |
| histamine | 1 mM | 0 |
| α-(methylamino) Isobutyric acid | 1 mM | 3 |
| (−)-norepinephrine | 1 mM | 0 |
| sarcosine | 10 μM | 23 |
|  | 100 μM | 64 |
|  | 1 mM | 100 |
| L-serine | 1 mM | 4 |

[a]COS-7 cells transfected with rB20a encoding the glycine transporter were incubated for 10 minutes (37° C.) with 50 nM [$^3$H]glycine and the indicated compounds. Non-specific uptake was determined with 1 mM glycine. Data show percent displacement of specific [$^3$H]glycine uptake.

Glycine is a substrate for multiple amino acid transport systems in various tissues, therefore it was important to determine the relationship of the cloned transporter to previously identified systems. Neither α-(methylamino) isobutyric acid (1 mM), a substrate for system A, nor L-serine (1 mM), a substrate for system ASC, significantly competed for [$^3$H]glycine uptake. Sarcosine (N-methylglycine) inhibited specific [$^3$H]glycine transport 23%, 64% and 100% at 10 μM, 100M, and 1 mM, respectively, consistent with an $IC_{50}$ of approximately 50 μM. The ethyl- and methyl-esters of glycine were less potent than glycine, inhibiting specific transport 32% and 42% at 1 mM, respectively; no inhibition was seen at 10 μM and 100 μM. Other agents tested did not compete for [$^3$H]glycine uptake. These data indicate that rB20a encodes a glycine-specific transporter.

Figure 5:
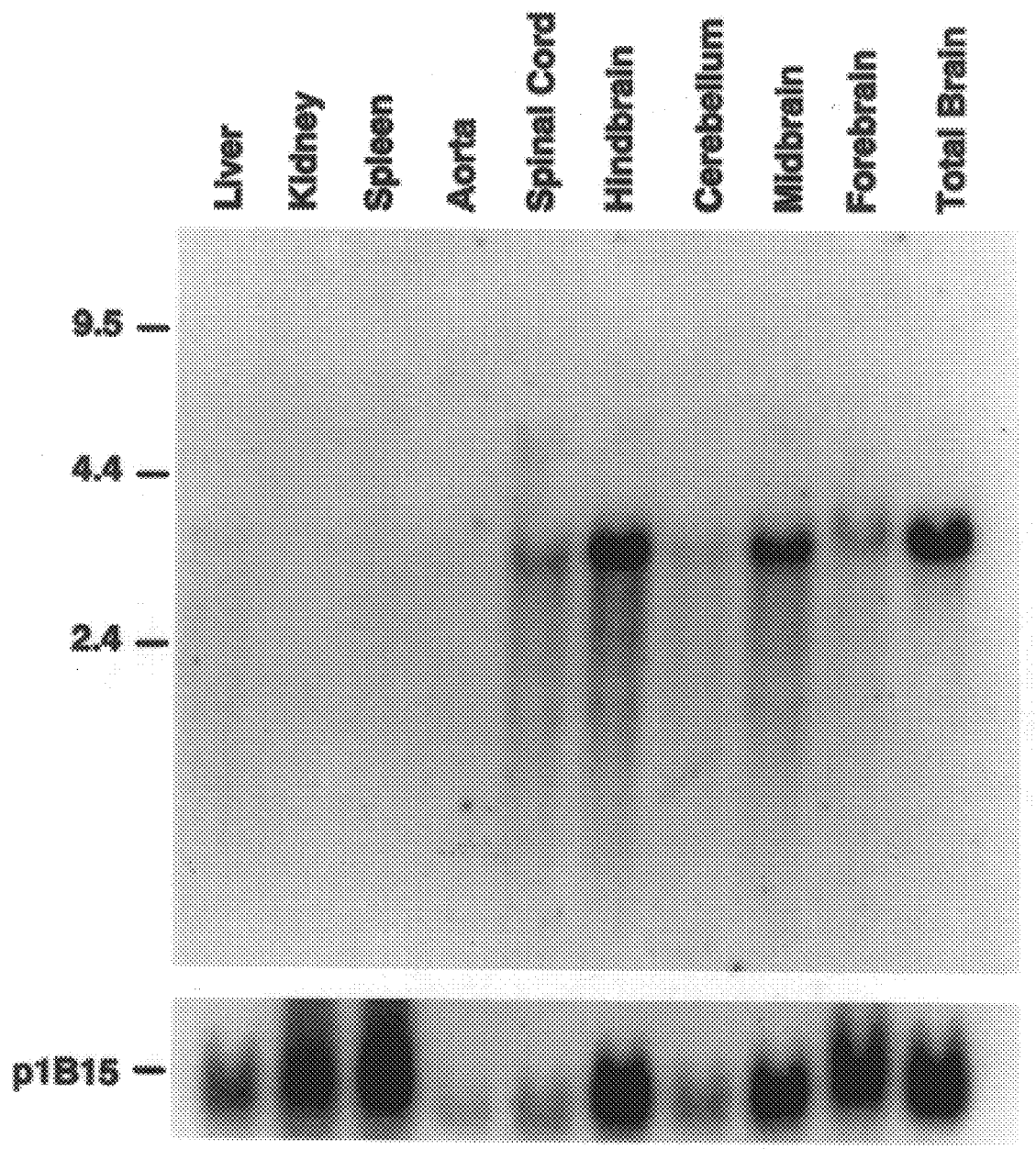
FIG. 5. Northern blot analysis of glycine transporter mRNA.

To define the distribution of the mRNA encoding the glycine transporter we carried out Northern blot analysis of total RNA isolated from a variety of rat brain regions and peripheral tissues (FIG. 5). A single transcript (≈3.8 kb) which hybridized at high stringency with the glycine transporter cDNA was present in all CNS samples, including total brain, midbrain, hind brain, cerebellum, and spinal cord, with lower levels in forebrain. Following normalization of RNA levels by reprobing with a cDNA encoding cyclophilin (Danielson et al., 1988), the adjusted levels of glycine mRNA in the spinal cord and cerebellum were determined to be roughly equivalent to those found in hindbrain and midbrain. The transcript was not detectable in spleen, kidney, or aorta. A very light signal was detected in liver; this reflects either cross-hybridization with a related gene, or extremely low expression of the glycine transporter mRNA. These data suggest that the glycine transporter mRNA is expressed primarily in the nervous system.

To more precisely determine the localization of the glycine transporter, in situ hybridization of specific antisense probes was examined in coronal sections of the rat CNS (FIG. 6). Glycine transporter mRNA was observed at all brain levels, though the distribution displayed considerable regional heterogeneity. Moderate to high levels of mRNA were detected in spinal cord, brain stem, and midbrain, areas in which the role of glycine in inhibitory neurotransmission is well established. The globus pallidus and hypothalamus were moderately labeled, whereas light labeling was observed in the thalamus and striatum; the substantia nigra was devoid of label. The neocortex displayed light, diffuse labeling at all rostro-caudal levels. Dense labeling was observed in the mitral cell layer of the olfactory bulb and the granular layer of the cerebellum. Surprisingly, heavy labeling was observed in the pyramidal cell layer of the hippocampal formation (dentate gyrus, CA1, CA2, and CA3) (FIG. 6), an area in which classical glycine receptors are absent or in low abundance (Malosio et al., 1991; van den Pol and Gorcs, 1988). Rather, the labeling pattern in the hippocampus corresponds to that of the glycine modulatory site of the NMDA receptor (Monoghan, 1990).

To obtain a cDNA clone encoding the human glycine transporter (hGlycine) we used PCR primers based on the nucleotide sequence of the rat glycine transporter cDNA to detect the presence of hGlycine in human cDNA libraries. PCR was carried out at a reduced annealing temperature to allow mismatches between rat and human sequences (see Experimental Procedures); amplified hGlycine sequences were detected by hybridization at low stringency with radiolabeled oligonucleotides representing the rat glycine transporter sequence. A human temporal cortex cDNA library (Stratagene) was identified and screened at low stringency with the same probes, resulting in isolation of a partial cDNA clone (hTC27a) containing the major portion of the coding region of hGlycine. The hGlycine nucleotide sequence from this clone and the deduced amino acid sequence based on translation of a long open reading frame is shown in FIG. 7. The sequence includes 936 base pairs of coding region (312 amino acids) and 45 base pairs of 5' untranslated region. Comparison with the rat glycine transporter amino acid sequence reveals 95% identity over the region encoded by the clone, which includes the initiating methionine (N-terminus) and predicted transmembrane domains 1–5 of the human glycine transporter. Compared with the rat, the N-terminus of the human glycine transporter is predicted to contain 14 additional amino acids based on a different predicted site for translation initiation in the human sequence.

Discussion

Despite their importance in synaptic transmission, our understanding of the molecular nature of neurotransmitter transporters has lagged behind that of neurotransmitter receptors. Our identification of a cDNA clone encoding a glycine transporter, together with the recent cloning of transporters for GABA (Guastella et al., 1990), norepinephrine (Pacholczyk et al., 1991), dopamine (Kilty et al., 1991; Shimada et al., 1991), and serotonin (Blakely et al., 1991; Hoffman et al., 1991), provides a framework for defining the structural features of this class of membrane proteins.

The glycine transporter cloned from rat brain displays striking sequence similarity to the other members of the transporter family. Alignment of the amino acid sequence of the glycine transporter with those of the GABA and norepinephrine transporters (FIG. 2) reveals multiple domains which are highly conserved within the family. Despite differing substrate specificities, over half of the residues shared between the GABA and norepinephrine carriers are also present in the glycine transporter, and the majority of these are common to all five cloned transporters. It seems unlikely that such regions are directly involved in substrate recognition, but rather may subserve a common transport function. A characteristic which distinguishes the neurotransmitter transporters from other similarly modeled nutrient transporters, such as the facilitated glucose carriers (Kayano et al., 1990), is the large extracellular loop between transmembrane domains 3 and 4, which has several potential glycosylation sites. Amino acid sequences in this loop and in transmembrane domains 9–11 are more divergent than in many other regions, raising the possibility that these domains contribute to specificity of substrate recognition.

In addition to its signalling roles, glycine also functions as an amino acid constituent of proteins in both neural and non-neural tissues. Northern blot analysis suggests that the cloned glycine transporter is neural-specific and thus is distinct from "system gly", a glycine-specific transport system present in various non-neural tissues such as hepatocytes (Christensen and Handlogten, 1981; Moseley et al., 1988) and red blood cells (Felipe et al., 1990). The pharmacological specificity of the cloned glycine transporter (Table 1) is similar to that observed for the high-affinity glycine transporter present in cultured glial cells (Zafra and Gimenez, 1989) and to the reconstituted transporter isolated from spinal cord (Lopez-Corcuera and Aragon, 1989), and clearly distinguishes it from two of the classical amino acid transporter systems, system A and system ASC (Christensen, 1984), both of which can transport glycine as well as other amino acids. Additionally, the affinity of the cloned transporter for glycine (Km=123 uM) is nearly identical to that of the high-affinity transporter present in glial cell cultures (95 uM; Zafra and Gimenez, 1989) and differs by only 2-fold from the high-affinity transporter in rat brain synaptosomes (50 uM; Mayor et al., 1981). Taken together, these data support a role for the cloned glycine transporter in neurotransmission, consistent with its high degree of structural similarity to other neurotransmitter transporters. The identification of a neural-specific high-affinity glycine transporter suggests that it may be possible to design selective, centrally acting glycine uptake inhibitors.

Localization studies of the mRNA for the glycine transporter reveal that it is not only present in spinal cord and brain stem, where it presumably participates in classical inhibition, but it is also extensively expressed in hippocampus and cortex, areas in which classical glycine .inhibitory receptors are thought to be absent or in low abundance (Malosio et al., 1991; van den Pol and Gorcs, 1988). Rather, these areas contain high levels of NMDA receptor-associated glycine binding sites (Monoghan, 1990; Moriyoshi et al., 1991; Kumar et al., 1991) suggesting that the glycine transporter modulates NMDA receptors and could serve to regulate cognitive processes such as memory storage. Our finding of high levels of glycine transporter mRNA in the hippocampal formation suggests that the endogenous level of glycine in the extracellular space may be modulated by the transporter. The ability to modulate glycine levels and thereby to modulate the functional effectiveness of the NMDA receptor may have importance for regulating higher nervous system processes.

Recently, a glycine transporter cDNA that is similar but not identical to that cloned by Smith et al. (1992) was cloned from both rat (Guastella et al., 1992) and mouse (Liu et al., 1992a). These isoforms may result from alternative splicing and could provide a means for regulating tissue-specific expression. In addition to those for glycine, several additional transporters have been cloned which exhibit significant sequence homology with previously cloned neurotransmitter transporters. cDNA and genomic clones representing the mouse homologues of the GABA transporter GAT-1 were recently reported (Liu et al., 1992). We recently reported the cloning and expression of two novel high-affinity GABA transporters from rat brain, designated GAT-2 and GAT-3 (Borden et al., 35 1992). A β-alanine-sensitive GABA transporter from rat brain has been cloned by Clark et al., (1992) that exhibits 100% amino acid identity with the rat GAT-3 sequence reported by Borden et al. (1992). A high-affinity L-proline transporter was reported by Fremeau et al. (1992), supporting a role for L-proline in excitatory neurotransmission. A rat cDNA identified as a choline transporter was reported by Mayser et al. (1992). A taurine transporter cDNA was recently cloned from dog kidney cells (Uchida et al., 1992) which is 90% identical to the rat taurine transporter amino acid sequence reported by Smith et al. (1992a). Finally, a cDNA encoding a mouse GABA transporter was recently cloned by Lopez-Corcuera et al. (1992); the transporter encoded by this cDNA is 88% identical to the dog betaine transporter (Yamauchi et al., 1992).

The use of human gene products in the process of drug development offers significant advantages over those of other species, which may not exhibit the same pharmacologic profiles. To facilitate this human target-based approach to drug design in the area of inhibitory amino acid transporters, we used the nucleotide sequence of the rat brain high-affinity glycine transporter (Smith et al., 1992) to clone the human glycine transporter. The cloning and expression of the human brain glycine transporter will allow comparison of its pharmacological profile with that of the rat glycine transporter, and also provide a means for understanding and predicting the mechanism of action of glycine uptake inhibitors as human therapeutics.

REFERENCES

Aprison, M. H. (1990). The discovery of the neurotransmitter role of glycine; in Glycine Transmission. (Ottersen, O. P. and Storm-Mathisen, J., ed), John Wiley and Sons, New York, pp. 1–24.

Becker, C.-M. (1990). Disorders of the inhibitory glycine receptor: the spastic mouse. FASEB. J. 4, 2767–2771.

Bennett, J. P, Jr., Mulder, A. H., and Snyder, S. H. (1974). Neurochemical correlates of synaptically active amino acids. *Life Sci*. 15, 1045–1056.

Blakely, R. D., Berson, H. E., Fremeau, Jr., R. T., Caron, M. G., Peek, M. M., Prince, H. K., and Bradley, C. C. (1991). Cloning and expression of a functional serotonin transporter from rat brain. *Nature* 354, 66–70.

Borden, L. A., K. E. Smith, P. R. Hartig, T. A. Branchek, and R. L. Weinshank (1992) *J. Biol. Chem.* 267, 21098–21104.

Christensen, H. N. (1984). Organic ion transport during seven decades. The amino acids. *Biochim. Biophys. Acta* 779, 255–269.

Christensen, H. N. and Handlogten, M. E. (1981). Role of system gly in glycine transport in monolayer cultures of liver cells. *Biochem. Biophys. Res. Comm.* 98, 102–107.

Clark, J. A., A. Y. Deutch, P. Z. Gallipoli, and S. G. Amara (1992) *Neuron* 9, 337–348.

Cohen, J. S. (1989) *Trends in Pharm. Sci.* 10, 435.

Collingridge, G. L. and Bliss, T. V. P. (1987). NMDA receptors-their role in long-term potentiation. *Trends Neurosci.* 10, 288–293.

Cortes, R. and Palacios, J. M. (1990). Autoradiographic mapping of glycine receptors by [$^3$H] strychnine binding; in Glycine Transmission (Ottersen, O. P. and Storm-Mathisen, J., ed), John Wiley and Sons, New York, pp.240–263.

Daly, E. C. (1990). The biochemistry of glycinergic neurons; in Glycine Transmission (Ottersen, O. P. and Storm-Mathisen, J., ed), John Wiley and Sons, New York, pp. 25–66.

Danielson, P. E., Forss-Petter, S., Brow, M. A., Calavetta, L., Douglass, J., Milner, R. J. and Sutcliffe, J. G. (1988). p1B15: A cDNA clone of the rat mRNA encoding cyclophilin. DNA 7, 261–267.

Debler, E. A. and Lajtha, A. (1987) J. Neurochem. 48, 1851–1856.

Feinberg, A. P., and Vogelstein, B. (1988). A technique for radiolabeling DNA restriction endonuclease fragments to high specific activity. *Anal. Biochem.* 132, 6–13.

Felipe, A., Vinas, O., and Remear, X. (1990). Changes in glycine and leucine transport during red cell maturation in the rat. Neurosci. Reports 10, 209–216.

Fletcher, E. J. Beart, P. M., and Lodge, D. (1990). Involvement of glycine in excitatory neurotransmission; in Glycine Transmission (Ottersen, O. P. and Storm-Mathisen, J., ed), John Wiley and Sons, New York, pp. 193–219.

Fremeau, R. T., Jr., M. G. Caron, and R. D. Blakely (1992) *Neuron* 8, 915–926.

Grenningloh, G., Rienitz, A., Schmitt, B., Methfessel, C., Zensen, M., Beyreuther, K., Gundelfinger, E. D., and Betz, H. (1987). The strychnine-binding subunit of the glycine receptor shows homology with nicotinic acetylcholine receptors. *Nature* 328, 215–220.

Guastella, J., N. Brecha, C. Wiegmann, H. A. Lester, and N. Davidson (1992) *Proc. Natl. Acad. Sci. USA* 89, 7189–7193.

Guastella, J., Nelson, N., Nelson, H., Czyzyk, L., Keynan, S., Miedel, M. C., Davidson, N., Lester, H. A., and Kanner, B. I. (1990). Cloning and expression of a rat brain GABA transporter. *Science* 249, 1303–6.

Gundlach, A. L. (1990). Disorder of the inhibitory glycine receptor: inherited myoclonus in Poll Hereford calves. FASEB J. 4, 2761–2766.

Handelmann, G. E., Nevins, M. E., Mueller, L. L., Arnolde, S. M. and Cordi, A. A. (1989). Milacemide, a glycine prodrug, enhances performance of learning tasks in normal and amnestic rodents. *Pharmacol., Biochem. and Behavior* 34, 823–828.

Hardy, J. A., Barton, A., Lofdahl, E., Cheetham, S. C., Johnston, G.A.R., and Dodd, P.R. (1986) J. Neurochem. 47, 460–467.

Hoffman, B. J., Mezey, E., and Brownstein, M. J. (1991). Cloning of a serotonin transporter affected by antidepressants. *Science* 254, 579–580.

Horn, A. S. (1990). Dopamine uptake: a review of progress in the past decade. *Prog. Neurobiol.* 34, 387–400.

International Patent Application Number WO 90/06047.

Johnson, J. W. and Ascher, P. (1987). Glycine potentiates the NMDA response in cultured mouse brain neurons. *Nature* 325, 529–531.

Kanner, B. I, and Shuldiner, S. (1987). Mechanism of transport and storage of neurotransmitters. *CRC crit. Rev. Biochem.* 22, 1–38.

Kayano, T., Burant, C. F., Fukumoto, H., Gould, G. W., Fan, Y.-S., Eddy, R. L., Byers, M. G., Shows, T. B., Seins, S., and Bell, G. I. (1990). Human facilitative glucose transporters: Isolation, functional characterization, and gene localization of cDNAs encoding an isoform (GLUT5) expressed in small intestine, kidney, muscle, and adipose tissue and an unusual glucose transporter pseudogene-like sequence (GLUT6). *J. Biol Chem.* 265, 13276–13282.

Kilberg, M. S. (1982) *J. Membrane. Biol.* 69, 1–12.

Kilty, J. E., Lorang D., and Amara, S. G. (1991). Cloning and expression of a cocaine-sensitive rat dopamine transporter. *Science* 254, 578–579.

Kumar, K. N., Tilakaratne, N., Johnson. P. S., Allen, A. E., and Michaelis, E. K. (1991). Cloning of the cDNA for the glutamate-binding subunit of an NMDA receptor complex. *Nature* 354, 70–73.

Liu, Q.-R., H. Nelson, S. Mandiyan, B. Lopez-Corcuera, and N. Nelson (1992a) FEBS Letters 305, 110–114.

Liu, Q.-R., S. Mandiyan, H. Nelson, and N. Nelson (1992) *Proc. Natl. Acad. Sci. USA* 89, 6639–6643.

Lopata, M. A., Cleveland, D. W., and Sollner-Webb, B. (1984). High-level expression of a chloramphenicol acetyltransferase gene by DEAE-dextran-mediated DNA transfection coupled with a dimethyl sulfoxide or glycerol shock treatment. *Nucl. Acids Res.* 12, 5707–5717.

Lopez-Corcuera, B and Aragon, C. (1989). Solubilization and reconstitution of the sodium- and chloride-coupled glycine transporter from rat spinal cord. *Eur. J. Biochem.* 181, 519–524.

Lopez-Corcuera, B., Q.-R. Liu, S. Mandiyan, H. Nelson, and N. Nelson (1992) *J. Biol. Chem.* 267, 17491–17493.

Low, M. J., Lechan, R. M., Hammer, R. E. et al. (1986) *Science* 231:1002–1004.

Malosio, M.-L., Marqueze-Pouey, B., Kuhse, J., and Betz, H. (1991). Widespread expression of glycine receptor subunit mRNAs in the adult and developing rat brain. *EMBO J.* 10, 2401–2409.

Maniatis, T., Fritsch, E. F., Sambrook, J. (1982) *Molecular Cloning*, Cold Spring Harbor Laboratory.

Mayor, F., Marvizon, J. G., Aragon, M. C., Gimenez, C., and Valdivieso, F. (1981). Glycine transport into plasma-membrane vesicles derived from rat brain synaptosomes. *Biochem. J.* 198, 535–541.

Mayser, W., P. Schloss, and H. Betz (1992) FEBS Letters 305, 31–36.

Monoghan, D. T. (1990). Glycine modulation of NMDA receptors: Autoradiographic studies; in Glycine.

Transmission (Ottersen, O. P. and Storm-Mathisen, J., ed), John Wiley and Sons, New York, pp.219–237.

Moriyoshi, K., Masu, M. Ishii, T., Shigemoto, R., Mizuno, N., Nakanishi, S. (1991). Molecular cloning and characterization of the rat NMDA receptor. *Nature* 354, 31–37.

Moseley, R., Ballatori, N., and Murphy, S.M. (1988). Na$^+$-glycine cotransport in canalicular liver plasma membrane vesicles. *Am. J. Physiol.* 255, G253–259.

Moseley, R., Ballatori, N., and Murphy, S. M. (1988) *Am. J. Physiol.* 255, G253–259.

Oberdick, J., Smeyne, R. J., Mann, J. R., Jackson, S. and Morgan, J. I. (1990) *Science* 248:223–226.

Pacholczyk, T., Blakely, R. D., and Amara, S. G. (1991). Expression cloning of a cocaine- and antidepressant-sensitive human noradrenaline transporter. *Nature* 350, 350–354.

Sanger, S. (1977). DNA sequencing with chain-terminating inhibitors. *Proc. Natl. Acad. Sci. USA* 74, 5463–5467.

Sanger, S. (1977) *Proc. Natl. Acad. Sci. USA* 74: 5463–5467.

Shimada, S., Kitayama, S., Lin, C.-L., Patel, A., Nanthakumaar, E., Gregor, P. Kuhar, M. and Uhl, G. (1991). Cloning and expression of a cocaine-sensitive dopamine transporter complementary DNA. *Science* 254, 576–578.

Smith, K. E., L. A. Borden, P. R. Hartig, T. A. Branchek, and R. L. Weinshank (1992) *Neuron* 8, 927–935.

Smith, K. E., L. A. Borden, C.-H.D. Wang, P. R. Hartig, T. A. Branchek, and R.L. Weinshank (1992a) *Mol. Pharm.* 42, 563–569.

Uchida, S., H. M. Kwon, A. Yamauchi, A. S. Preston, F. Marumo, and J. Handler (1992) *Proc. Natl. Acad. Sci. USA* 89, 8230–8234.

van den Pol, A. N. and Gorcs, T. (1988). Glycine and glycine receptor immunoreactivity in brain and spinal cord. *J. Neuroscience* 8, 472–492.

Weintraub, H. M. (1990) Sci. Am. January p. 40.

Yamauchi, A., S. Uchida, H. M. Kwon, A. S. Preston, R. B. Robey, A. Garcia-Perez, M. B. Burg, and J. S. Handler (1992) *J. Biol. Chem.* 267, 649–652.

Zafra, F. and Gimenez, C. (1986) Br. Res. 397, 108–116.

Zafra, F. and Gimenez, C. (1989). Characteristics and adaptive regulation of glycine transport in cultured glial cells. *Biochem. J.* 258, 403–408.

---

What is claimed is:

1. A method for determining whether a compound not known to be capable of specifically binding to a glycine transporter can specifically bind to such glycine transporter, which comprises contacting mammalian cells expressing on their cell surface a human or rat glycine transporter, wherein the transporter is expressed by cDNA transfected into the cell using a plasmid expression vector and wherein the human glycine transporter comprises the amino acid sequence set forth in SEQ ID NO: 6 and the rat glycine transporter comprises the amino acid sequence set forth in SEQ ID NO: 2, with the compound under conditions suitable for binding, and detecting specific binding of the compound to the human or rat glycine transporter.

2. A method for determining whether a compound not known to be capable of specifically binding to a glycine transporter can specifically bind to such glycine transporter, which comprises contacting a membrane preparation from mammalian cells expressing on their cell surface a human or rat glycine transporter, wherein the transporter is expressed by cDNA transfected into the cell using a plasmid expression vector and wherein the human glycine transporter comprises the amino acid sequence set forth in SEQ ID NO: 6 and the rat glycine transporter comprises the amino acid sequence set forth in SEQ ID NO: 2, with the chemical compound under conditions suitable for binding, and detecting specific binding of the chemical compound to the human or rat glycine transporter.

3. A method involving competitive binding for identifying a first compound which specifically binds to a glycine transporter, which comprises separately contacting mammalian cells expressing on their cell surface a human or rat glycine transporter, wherein the transporter is expressed by cDNA transfected into the cell using a plasmid expression vector and wherein the human glycine transporter comprises the amino acid sequence set forth in SEQ ID NO: 6 and the rat glycine transporter comprises the amino acid sequence set forth in SEQ ID NO: 2, with both the first compound and a second compound known to specifically bind to the transporter, and with only the second compound, under conditions suitable for binding of both compounds, and detecting specific binding of the first compound to the human or rat glycine transporter, a decrease in the binding of the second compound to the human or rat glycine transporter in the presence of the first compound indicating that the first compound binds to the human or rat glycine transporter.

4. A method involving competitive binding for identifying a first compound which specifically binds to a glycine transporter, which comprises separately contacting a membrane preparation from mammalian cells expressing on their cell surface a human or rat glycine transporter, wherein the transporter is expressed by cDNA transfected into the cell using a plasmid expression vector and wherein the human glycine transporter comprises the amino acid sequence set forth in SEQ ID NO: 6 and the rat glycine transporter comprises the amino acid sequence set forth in SEQ ID NO: 2, with both the first compound and a second compound known to specifically bind to the transporter, and with only the second compound, under conditions suitable for binding of both compounds, and detecting specific binding of the first compound to the human and rat glycine transporter, a decrease in the binding of the second compound to the human or rat glycine transporter in the presence of the first compound indicating that the first compound binds to the human or rat glycine transporter.

5. A method for identifying a compound which specifically binds to and inhibits a glycine transporter, which comprises separately contacting mammalian cells expressing on their cell surface a human or rat glycine transporter, wherein the transporter is expressed by cDNA transfected into the cell using a plasmid expression vector and wherein the human glycine transporter comprises the amino acid sequence set forth in SEQ ID NO: 6 and the rat glycine transporter comprises the amino acid sequence set forth in SEQ ID NO: 2, with both the compound and with a substrate for the transporter, and with only the substrate, under conditions suitable for binding and transport of the substrate, and detecting transport of the substrate, a decrease in the transport of the substrate by the human or rat glycine transporter in the presence of the compound indicating that the compound binds to and inhibits the human or rat glycine transporter.

6. A method for identifying a compound which specifically binds to and activates a glycine transporter, which comprises separately contacting mammalian cells expressing on their cell surface a human or rat glycine transporter, wherein the transporter is expressed by cDNA transfected into the cell using a plasmid expression vector and wherein the human glycine transporter comprises the amino acid sequence set forth in SEQ ID NO: 6 and the rat glycine transporter comprises the amino acid sequence set forth in SEQ ID NO: 2, with both the compound and with a substrate for the transporter, and with only the substrate, under conditions suitable for binding and transport of the substrate, and detecting transport of the substrate, an increase in the transport of the substrate by the human or rat glycine transporter in the presence of the compound indicating that the compound binds to and activates the human or rat glycine transporter.

7. A process of claim 1, 2, 3, 4, 5, or 6, wherein the mammalian cell is a non-neuronal cell.

8. A process of claim 7, wherein the non-neuronal cell is a Cos-7 cell.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2121 base pairs
      (B) TYPE: nucleic acid
      (C) STRANDEDNESS: both
      (D) TOPOLOGY: unknown (ii) MOLECULE TYPE: cDNA (iii) HYPOTHETICAL: N (iv) ANTI-SENSE: N (vi) ORIGINAL SOURCE:
      (A) ORGANISM: RAT GLYCINE TRANSPORTER
      (G) CELL TYPE: MAMMALIAN
      (H) CELL LINE: COS7

(vii) IMMEDIATE SOURCE:
      (B) CLONE: rB20a (ix) FEATURE:
    (A) NAME/KEY: CDS
    (B) LOCATION: 62..1975
    (D) OTHER INFORMATION:

(xi) SEQUENCE DESCRIPTION: SEQ ID NO:1:

```
GGAGCTGGCA GAGGTGTGAA TGAGCGGCTG AGACACTCGT GCTTTGAGTG CTCTTCCCAG        60
GATGGCTGTG GCTCACGGAC CTGTGGCCAC CTCTTCCCCA GAACAGAATG GTGCTGTGCC       120
CAGCGAGGCC ACCAAGAAGG ACCAGAACCT CACACGGGGC AACTGGGGCA ACCAGATCGA       180
GTTTGTACTG ACGAGCGTGG GCTATGCCGT GGGCCTGGGC AATGTGTGGC GTTTCCCATA       240
CCTCTGCTAT CGCAACGGGG GAGGCGCCTT CATGTTTCCC TACTTCATCA TGCTGGTCTT       300
CTGCGGCATT CCTCTCTTCT TCATGGAGCT CTCCTTCGGC CAGTTTGCAA GCCAGGGCTG       360
CCTGGGGGTC TGGAGGATCA GCCCCATGTT CAAAGGCGTG GGCTATGGTA TGATGGTGGT       420
GTCCACGTAC ATCGGTATCT ACTACAACGT GGTCATCTGC ATCGCCTTCT ACTACTTCTT       480
CTCGTCCATG ACGCATGTGC TGCCCTGGGC TTACTGCAAT AATCCCTGGA ACACACCCGA       540
CTGTGCCGGT GTGCTGGATG CTTCCAATCT CACCAATGGC TCCCGGCCCA CTGCCCTGTC       600
TGGCAACCTG TCTCACCTGT TCAACTACAC CTTGCAAAGG ACCAGCCCCA GTGAGGAGTA       660
CTGGAGGCTG TATGTGCTGA AGCTGTCGGA TGACATTGGA GATTTTGGAG AAGTGCGGCT       720
TCCTCTCCTA GGCTGCCTTG GCGTCTCCTG GGTGGTTGTC TTCCTCTGCC TCATTCGAGG       780
AGTCAAGTCT TCAGGGAAAG TGGTGTACTT CACGGCCACA TTTCCCTATG TGGTGCTGAC       840
CATTCTGTTT GTTCGTGGAG TGACCCTGGA AGGAGCCTTC ACGGGTATCA TGTACTACCT       900
GACCCCAAAG TGGGACAAGA TCCTGGAGGC CAAGGTGTGG GGGGATGCAG CCTCTCAGAT       960
CTTCTATTCC CTGGGCTGTG CATGGGGTGG CCTCATCACC ATGGCATCCT ACAACAAATT      1020
CCACAACAAC TGCTACCGGG ACAGCGTCAT CATCAGCATC ACCAATTGTG CTACCAGTGT      1080
CTATGCTGGC TTCGTCATCT TCTCTATCCT AGGCTTCATG GCCAATCACC TGGGTGTGGA      1140
TGTGTCTCGG GTGGCAGACC ACGGGCCCGG GCTAGCTTTC GTGGCTTACC CCGAGGCTCT      1200
CACACTGCTT CCCATCTCCC CGCTCTGGTC CTTGCTGTTT TTCTTCATGC TCATCCTGCT      1260
GGGACTCGGT ACTCAGTTCT GCCTCCTGGA GACCCTAGTC ACTGCCATTG TGGATGAGGT      1320
GGGGAATGAG TGGATTCTGC AGAAGAAGAC CTACGTGACC TTGGGTGTGG CTGTGGCTGG      1380
CTTCTTGCTG GGTATCCCTC TTACCAGCCA GGCGGGCATC TACTGGCTGC TGTTGATGGA      1440
CAACTACGCA GCCAGCTTCT CCTTGGTTGT CATCTCCTGC ATCATGTGCG TGTCCATCAT      1500
GTATATCTAT GGGCACCGGA ACTACTTCCA GGACATTCAG ATGATGCTGG GGTTCCCACC      1560
GCCTCTCTTC TTCCAGATCT GTTGGCGTTT TGTCTCTCCC ACTATCATCT TTTTCATTCT      1620
CATCTTCACG GTGATCCAGT ACCGGCCAAT CACTTACAAC CACTACCAGT ACCCAGGCTG      1680
GGCTGTGGCC ATCGGCTTCC TCATGGCTTT GTCGTCTGTC ATCTGCATCC CATTGTACGC      1740
ATTGTTCCAG CTCTGCCGCA CAGATGGGGA CACACTTCTT CAGCGTTTGA AAAATGCCAC      1800
AAAGCCAAGC AGAGACTGGG GCCCTGCCCT CCTGGAGCAC CGGACTGGGC GCTATGCCCC      1860
CACTACAACC CCCTCTCCTG AAGATGGGTT TGAGGTTCAG CCACTGCACC GGACAAGGC       1920
CCAGATCCCC ATCGTGGGCA GTAACGGCTC CAGCCGCCTC CAGGACTCCC GGATATGAGC      1980
ACAGTTGTTG CAAGGGGAGA AGCCCCACCC AACCCTTGCT CCTACCACAG AGACTGAGGA      2040
GGTGGTGGAC CGGTGTGACT GCCTGCCCCA TCATGCCCTG GCCAGGGTGG CTGCTGTCAC      2100
CTTGGCCACC ACTGCTCATG T                                                2121
```

(2) INFORMATION FOR SEQ ID NO:2:

(i) SEQUENCE CHARACTERISTICS:
        (A) LENGTH: 638 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Val Ala His Gly Pro Val Ala Thr Ser Ser Pro Glu Gln Asn
 1               5                  10                  15

Gly Ala Val Pro Ser Glu Ala Thr Lys Lys Asp Gln Asn Leu Thr Arg
             20                  25                  30

Gly Asn Trp Gly Asn Gln Ile Glu Phe Val Leu Thr Ser Val Gly Tyr
         35                  40                  45

Ala Val Gly Leu Gly Asn Val Trp Arg Phe Pro Tyr Leu Cys Tyr Arg
     50                  55                  60

Asn Gly Gly Gly Ala Phe Met Phe Pro Tyr Phe Ile Met Leu Val Phe
 65                  70                  75                  80

Cys Gly Ile Pro Leu Phe Phe Met Glu Leu Ser Phe Gly Gln Phe Ala
                 85                  90                  95

Ser Gln Gly Cys Leu Gly Val Trp Arg Ile Ser Pro Met Phe Lys Gly
            100                 105                 110

Val Gly Tyr Gly Met Met Val Val Ser Thr Tyr Ile Gly Ile Tyr Tyr
        115                 120                 125

Asn Val Val Ile Cys Ile Ala Phe Tyr Tyr Phe Phe Ser Ser Met Thr
    130                 135                 140

His Val Leu Pro Trp Ala Tyr Cys Asn Asn Pro Trp Asn Thr Pro Asp
145                 150                 155                 160

Cys Ala Gly Val Leu Asp Ala Ser Asn Leu Thr Asn Gly Ser Arg Pro
                165                 170                 175

Thr Ala Leu Ser Gly Asn Leu Ser His Leu Phe Asn Tyr Thr Leu Gln
            180                 185                 190

Arg Thr Ser Pro Ser Glu Glu Tyr Trp Arg Leu Tyr Val Leu Lys Leu
        195                 200                 205

Ser Asp Asp Ile Gly Asp Phe Gly Glu Val Arg Leu Pro Leu Leu Gly
    210                 215                 220

Cys Leu Gly Val Ser Trp Val Val Phe Leu Cys Leu Ile Arg Gly
225                 230                 235                 240

Val Lys Ser Ser Gly Lys Val Val Tyr Phe Thr Ala Thr Phe Pro Tyr
                245                 250                 255

Val Val Leu Thr Ile Leu Phe Val Arg Gly Val Thr Leu Glu Gly Ala
            260                 265                 270

Phe Thr Gly Ile Met Tyr Tyr Leu Thr Pro Lys Trp Asp Lys Ile Leu
        275                 280                 285

Glu Ala Lys Val Trp Gly Asp Ala Ala Ser Gln Ile Phe Tyr Ser Leu
    290                 295                 300

Gly Cys Ala Trp Gly Gly Leu Ile Thr Met Ala Ser Tyr Asn Lys Phe
305                 310                 315                 320

His Asn Asn Cys Tyr Arg Asp Ser Val Ile Ile Ser Ile Thr Asn Cys
                325                 330                 335

Ala Thr Ser Val Tyr Ala Gly Phe Val Ile Phe Ser Ile Leu Gly Phe
            340                 345                 350

Met Ala Asn His Leu Gly Val Asp Val Ser Arg Val Ala Asp His Gly
```

-continued

```
                355                 360                 365
Pro Gly Leu Ala Phe Val Ala Tyr Pro Glu Ala Leu Thr Leu Leu Pro
            370                 375                 380
Ile Ser Pro Leu Trp Ser Leu Leu Phe Phe Met Leu Ile Leu Leu Leu
385                 390                 395                 400
Gly Leu Gly Thr Gln Phe Cys Leu Leu Glu Thr Leu Val Thr Ala Ile
                405                 410                 415
Val Asp Glu Val Gly Asn Glu Trp Ile Leu Gln Lys Lys Thr Tyr Val
            420                 425                 430
Thr Leu Gly Val Ala Val Ala Gly Phe Leu Leu Gly Ile Pro Leu Thr
            435                 440                 445
Ser Gln Ala Gly Ile Tyr Trp Leu Leu Leu Met Asp Asn Tyr Ala Ala
            450                 455                 460
Ser Phe Ser Leu Val Val Ile Ser Cys Ile Met Cys Val Ser Ile Met
465                 470                 475                 480
Tyr Ile Tyr Gly His Arg Asn Tyr Phe Gln Asp Ile Gln Met Met Leu
                485                 490                 495
Gly Phe Pro Pro Pro Leu Phe Phe Gln Ile Cys Trp Arg Phe Val Ser
            500                 505                 510
Pro Thr Ile Ile Phe Phe Ile Leu Ile Phe Thr Val Ile Gln Tyr Arg
            515                 520                 525
Pro Ile Thr Tyr Asn His Tyr Gln Tyr Pro Gly Trp Ala Val Ala Ile
            530                 535                 540
Gly Phe Leu Met Ala Leu Ser Ser Val Ile Cys Ile Pro Leu Tyr Ala
545                 550                 555                 560
Leu Phe Gln Leu Cys Arg Thr Asp Gly Asp Thr Leu Leu Gln Arg Leu
                565                 570                 575
Lys Asn Ala Thr Lys Pro Ser Arg Asp Trp Gly Pro Ala Leu Leu Glu
            580                 585                 590
His Arg Thr Gly Arg Tyr Ala Pro Thr Thr Thr Pro Ser Pro Glu Asp
            595                 600                 605
Gly Phe Glu Val Gln Pro Leu His Pro Asp Lys Ala Gln Ile Pro Ile
        610                 615                 620
Val Gly Ser Asn Gly Ser Ser Arg Leu Gln Asp Ser Arg Ile
625                 630                 635

(2) INFORMATION FOR SEQ ID NO:3:

(i) SEQUENCE CHARACTERISTICS:
        (A) LENGTH: 617 amino acids
        (B) TYPE: amino acid
        (D) TOPOLOGY: linear (ii) MOLECULE TYPE: protein (iii) HYPOTHETICAL: N (v) FRAGMENT TYPE: internal (vi) ORIGINAL SOURCE:
        (A) ORGANISM: HUMAN NORADRENALINE TRANSPORTER (xi) SEQUENCE DESCRIPTION: SEQ ID NO:3:

Met Leu Leu Ala Arg Met Asn Pro Gln Val Gln Pro Glu Asn Asn Gly
1               5                   10                  15
Ala Asp Thr Gly Pro Glu Gln Pro Leu Arg Ala Arg Lys Thr Ala Glu
            20                  25                  30
Leu Leu Val Val Lys Glu Arg Asn Gly Val Gln Cys Leu Leu Ala Pro
```

-continued

```
                35                  40                  45
Arg Asp Gly Asp Ala Gln Pro Arg Glu Thr Trp Gly Lys Lys Ile Asp
 50                  55                  60
Phe Leu Leu Ser Val Val Gly Phe Ala Val Asp Leu Ala Asn Val Trp
 65                  70                  75                  80
Arg Phe Pro Tyr Leu Cys Tyr Lys Asn Gly Gly Ala Phe Leu Ile
                 85                  90                  95
Pro Tyr Thr Leu Phe Leu Ile Ile Ala Gly Met Pro Leu Phe Tyr Met
                100                 105                 110
Glu Leu Ala Leu Gly Gln Tyr Asn Arg Glu Gly Ala Ala Thr Val Trp
                115                 120                 125
Lys Ile Cys Pro Phe Phe Lys Gly Val Gly Tyr Ala Val Ile Leu Ile
130                 135                 140
Ala Leu Tyr Val Gly Phe Tyr Tyr Asn Val Ile Ile Ala Trp Ser Leu
145                 150                 155                 160
Tyr Tyr Leu Phe Ser Ser Phe Thr Leu Asn Leu Pro Trp Thr Asp Cys
                165                 170                 175
Gly His Thr Trp Asn Ser Pro Asn Cys Thr Asp Pro Lys Leu Leu Asn
                180                 185                 190
Gly Ser Val Leu Gly Asn His Thr Lys Tyr Ser Lys Tyr Lys Phe Thr
                195                 200                 205
Pro Ala Ala Glu Phe Tyr Glu Arg Gly Val Leu His Leu His Glu Ser
                210                 215                 220
Ser Gly Ile His Asp Ile Gly Leu Pro Gln Trp Gln Leu Leu Leu Cys
225                 230                 235                 240
Leu Met Val Val Ile Val Leu Tyr Phe Ser Leu Trp Lys Gly Val
                245                 250                 255
Lys Thr Ser Gly Lys Val Val Trp Ile Thr Ala Thr Leu Pro Tyr Phe
                260                 265                 270
Val Leu Phe Val Leu Leu Val His Gly Val Thr Leu Pro Gly Ala Ser
                275                 280                 285
Asn Gly Ile Asn Ala Tyr Leu His Ile Asp Phe Tyr Arg Leu Lys Glu
                290                 295                 300
Ala Thr Val Trp Ile Asp Ala Ala Thr Gln Ile Phe Phe Ser Leu Gly
305                 310                 315                 320
Ala Gly Phe Gly Val Leu Ile Ala Phe Ala Ser Tyr Asn Lys Phe Asp
                325                 330                 335
Asn Asn Cys Tyr Arg Asp Ala Leu Leu Thr Ser Ser Ile Asn Cys Ile
                340                 345                 350
Thr Ser Phe Val Ser Gly Phe Ala Ile Phe Ser Ile Leu Gly Tyr Met
                355                 360                 365
Ala His Glu His Lys Val Asn Ile Glu Asp Val Ala Thr Glu Gly Ala
                370                 375                 380
Gly Leu Val Phe Ile Leu Tyr Pro Glu Ala Ile Ser Thr Leu Ser Gly
385                 390                 395                 400
Ser Thr Phe Trp Ala Val Val Phe Phe Val Met Leu Leu Ala Leu Gly
                405                 410                 415
Leu Asp Ser Ser Met Gly Gly Met Glu Ala Val Ile Thr Gly Leu Ala
                420                 425                 430
Asp Asp Phe Gln Val Leu Lys Arg His Arg Lys Leu Phe Thr Phe Gly
                435                 440                 445
Val Thr Phe Ser Thr Phe Leu Leu Ala Leu Phe Cys Ile Thr Lys Gly
450                 455                 460
```

```
Gly Ile Tyr Val Leu Thr Leu Leu Asp Thr Phe Ala Ala Gly Thr Ser
465                 470                 475                 480

Ile Leu Phe Ala Val Leu Met Glu Ala Ile Gly Val Ser Trp Phe Tyr
                485                 490                 495

Gly Val Asp Arg Phe Ser Asn Asp Ile Gln Gln Met Met Gly Phe Arg
            500                 505                 510

Pro Gly Leu Tyr Trp Arg Leu Cys Trp Lys Phe Val Ser Pro Ala Phe
        515                 520                 525

Leu Leu Phe Val Val Val Ser Ile Ile Asn Phe Lys Pro Leu Thr
    530                 535                 540

Tyr Asp Asp Tyr Ile Phe Pro Pro Trp Ala Asn Trp Val Gly Trp Gly
545                 550                 555                 560

Ile Ala Leu Ser Ser Met Val Leu Val Pro Ile Tyr Val Ile Tyr Lys
                565                 570                 575

Phe Leu Ser Thr Gln Gly Ser Leu Trp Glu Arg Leu Ala Tyr Gly Ile
            580                 585                 590

Thr Pro Glu Asn Glu His His Leu Val Ala Gln Arg Asp Ile Arg Gln
        595                 600                 605

Phe Gln Leu Gln His Trp Leu Ala Ile
    610                 615
```

(2) INFORMATION FOR SEQ ID NO:4:

(i) SEQUENCE CHARACTERISTICS:
        (A) LENGTH: 599 amino acids
        (B) TYPE: amino acid
        (D) TOPOLOGY: linear (ii) MOLECULE TYPE: protein (iii) HYPOTHETICAL: N (v) FRAGMENT TYPE: internal (vi) ORIGINAL SOURCE:
        (A) ORGANISM: RAT GABA TRANSPORTER (GAT-1)

(xi) SEQUENCE DESCRIPTION: SEQ ID NO:4:

```
Met Ala Thr Asp Asn Ser Lys Val Ala Asp Gly Gln Ile Ser Thr Glu
1               5                   10                  15

Val Ser Glu Ala Pro Val Ala Ser Asp Lys Pro Lys Thr Leu Val Val
                20                  25                  30

Lys Val Gln Lys Lys Ala Gly Asp Leu Pro Asp Arg Asp Thr Trp Lys
            35                  40                  45

Gly Arg Phe Asp Phe Leu Met Ser Cys Val Gly Tyr Ala Ile Gly Leu
        50                  55                  60

Gly Asn Val Trp Arg Phe Pro Tyr Leu Cys Gly Lys Asn Gly Gly Gly
65                  70                  75                  80

Ala Phe Leu Ile Pro Tyr Phe Leu Thr Leu Ile Phe Ala Gly Val Pro
                85                  90                  95

Leu Phe Leu Leu Glu Cys Ser Leu Gly Gln Tyr Thr Ser Ile Gly Gly
            100                 105                 110

Leu Gly Val Trp Lys Leu Ala Pro Met Phe Lys Gly Val Gly Leu Ala
        115                 120                 125

Ala Ala Val Leu Ser Phe Trp Leu Asn Ile Tyr Tyr Ile Val Ile Ile
    130                 135                 140

Ser Trp Ala Ile Tyr Tyr Leu Tyr Asn Ser Phe Thr Thr Thr Leu Pro
145                 150                 155                 160
```

-continued

```
Trp Lys Gln Cys Asp Asn Pro Trp Asn Thr Asp Arg Cys Phe Ser Asn
                165                 170                 175
Tyr Ser Leu Val Asn Thr Thr Asn Met Thr Ser Ala Val Val Glu Phe
            180                 185                 190
Trp Glu Arg Asn Met His Gln Met Thr Asp Gly Leu Asp Lys Pro Gly
        195                 200                 205
Gln Ile Arg Trp Pro Leu Ala Ile Thr Leu Ala Ile Ala Trp Val Leu
    210                 215                 220
Val Tyr Phe Cys Ile Trp Lys Gly Val Gly Trp Thr Gly Lys Val Val
225                 230                 235                 240
Tyr Phe Ser Ala Thr Tyr Pro Tyr Ile Met Leu Ile Ile Leu Phe Phe
                245                 250                 255
Arg Gly Val Thr Leu Pro Gly Ala Lys Glu Gly Ile Leu Phe Tyr Ile
            260                 265                 270
Thr Pro Asn Phe Arg Lys Leu Ser Asp Ser Glu Val Trp Leu Asp Ala
        275                 280                 285
Ala Thr Gln Ile Phe Phe Ser Tyr Gly Leu Gly Leu Gly Ser Leu Ile
    290                 295                 300
Ala Leu Gly Ser Tyr Asn Ser Phe His Asn Asn Val Tyr Arg Asp Ser
305                 310                 315                 320
Ile Ile Val Cys Cys Ile Asn Ser Cys Thr Ser Met Phe Ala Gly Phe
                325                 330                 335
Val Ile Phe Ser Ile Val Gly Phe Met Ala His Val Thr Lys Arg Ser
            340                 345                 350
Ile Ala Asp Val Ala Ala Ser Gly Pro Gly Leu Ala Phe Leu Ala Tyr
        355                 360                 365
Pro Glu Ala Val Thr Gln Leu Pro Ile Ser Pro Leu Trp Ala Ile Leu
    370                 375                 380
Phe Phe Ser Met Leu Leu Met Leu Gly Ile Asp Ser Gln Phe Cys Thr
385                 390                 395                 400
Val Glu Gly Phe Ile Thr Ala Leu Val Asp Glu Tyr Pro Arg Leu Leu
                405                 410                 415
Arg Asn Arg Arg Glu Leu Phe Ile Ala Ala Val Cys Ile Val Ser Tyr
            420                 425                 430
Leu Ile Gly Leu Ser Asn Ile Thr Gln Gly Gly Ile Tyr Val Phe Lys
        435                 440                 445
Leu Phe Asp Tyr Tyr Ser Ala Ser Gly Met Ser Leu Leu Phe Leu Val
    450                 455                 460
Phe Phe Glu Cys Val Ser Ile Ser Trp Phe Tyr Gly Val Asn Arg Phe
465                 470                 475                 480
Tyr Asp Asn Ile Gln Glu Met Val Gly Ser Arg Pro Cys Ile Trp Trp
                485                 490                 495
Lys Leu Cys Trp Ser Phe Phe Thr Pro Ile Ile Val Ala Gly Val Phe
            500                 505                 510
Leu Phe Ser Ala Val Gln Met Thr Pro Leu Thr Met Gly Ser Tyr Val
        515                 520                 525
Phe Pro Lys Trp Gly Gln Gly Val Gly Trp Leu Met Ala Leu Ser Ser
    530                 535                 540
Met Val Leu Ile Pro Gly Tyr Met Ala Tyr Met Phe Leu Thr Leu Lys
545                 550                 555                 560
Gly Ser Leu Lys Gln Arg Leu Gln Val Met Ile Gln Pro Ser Glu Asp
                565                 570                 575
```

Ile Val Arg Pro Glu Asn Gly Pro Glu Gln Pro Gln Ala Gly Ser Ser
            580                 585                 590

Ala Ser Lys Glu Ala Tyr Ile
        595

(2) INFORMATION FOR SEQ ID NO:5:

(i) SEQUENCE CHARACTERISTICS:
        (A) LENGTH: 981 base pairs
        (B) TYPE: nucleic acid
        (C) STRANDEDNESS: both
        (D) TOPOLOGY: unknown (ii) MOLECULE TYPE: cDNA (iii) HYPOTHETICAL: N (iv) ANTI-SENSE: N (vi) ORIGINAL SOURCE:
        (A) ORGANISM: HUMAN GLYCINE TRANSPORTER (vii) IMMEDIATE SOURCE:
        (B) CLONE: pBluescript-hTC27a (ix) FEATURE:
        (A) NAME/KEY: CDS
        (B) LOCATION: 46..981
        (D) OTHER INFORMATION:

(xi) SEQUENCE DESCRIPTION: SEQ ID NO:5:

```
GGCAGGGGAT GCGTCAGTGT CGCGCTGGAG CTGGCAGAGG TGTGAATGAG CGGCGGAGAC     60
ACGCGGGCTG CGATCGCTCG CCCCAGGATG GCCGCGGCTC ATGGACCTGT GGCCCCCTCT    120
TCCCCAGAAC AGAATGGTGC TGTGCCCAGC GAGGCCACCA AGAGGGACCA GAACCTCAAA    180
CGGGGCAACT GGGCAACCA GATCGAGTTT GTACTGACGA GCGTGGGCTA TGCCGTGGGC     240
CTGGGCAATG TCTGGCGCTT CCCATACCTC TGCTATCGCA ACGGGGGAGG CGCCTTCATG    300
TTCCCCTACT TCATCATGCT CATCTTCTGC GGGATCCCCC TCTTCTTCAT GGAGCTCTCC    360
TTCGGCCAGT TTGCAAGCCA GGGGTGCCTG GGGTCTGGA GGATCAGCCC CATGTTCAAA     420
GGAGTGGGCT ATGGTATGAT GGTGGTGTCC ACCTACATCG GCATCTACTA CAATGTGGTC    480
ATCTGCATCG CCTTCTACTA CTTCTTCTCG TCCATGACGA ACGTGCTGCC CTGGGCCTAC    540
TGCAATAACC CCTGGAACAC GCATGACTGC GCCGGTGTAC TGGACGCCTC CAACCTCACC    600
AATGGCTCTC GGCCAGCCGC CTTGCCCAGC AACCTCTCCC ACCTGCTCAA CCACAGCCTC    660
CAGAGGACCA GCCCCAGCGA GGAGTACTGG AGGCTGTACG TGCTGAAGCT GTCAGATGAC    720
ATTGGGAACT TTGGGGAGGT GCGGCTGCCC CTCCTTGGCT GCCTCGGTGT CTCCTGGTTG    780
GTCGTCTTCC TCTGCCTCAT CCGAGGGGTC AAGTCTTCAG GGAAAGTGGT GTACTTCACG    840
GCCACGTTCC CCTACGTGGT GCTGACCATT CTGTTTGTCC GCGGAGTGAC CCTGGAGGGA    900
GCCTTTGACG GCATCATGTA CTACCTAACC CCGCAGTGGG ACAAGATCCT GGAGGCCAAG    960
GTGTGGGGTG ATGCTGCCTC C                                             981
```

(2) INFORMATION FOR SEQ ID NO:6:

(i) SEQUENCE CHARACTERISTICS:
        (A) LENGTH: 312 amino acids
        (B) TYPE: amino acid
        (D) TOPOLOGY: linear (ii) MOLECULE TYPE: protein (xi) SEQUENCE DESCRIPTION: SEQ ID NO:6:

Met Ser Gly Gly Asp Thr Arg Ala Ala Ile Ala Arg Pro Arg Met Ala
 1               5                  10                  15

Ala Ala His Gly Pro Val Ala Pro Ser Ser Pro Glu Gln Asn Gly Ala
             20                  25                  30

Val Pro Ser Glu Ala Thr Lys Arg Asp Gln Asn Leu Lys Arg Gly Asn
             35                  40                  45

Trp Gly Asn Gln Ile Glu Phe Val Leu Thr Ser Val Gly Tyr Ala Val
         50                  55                  60

Gly Leu Gly Asn Val Trp Arg Phe Pro Tyr Leu Cys Tyr Arg Asn Gly
 65                  70                  75                  80

Gly Gly Ala Phe Met Phe Pro Tyr Phe Ile Met Leu Ile Phe Cys Gly
                 85                  90                  95

Ile Pro Leu Phe Phe Met Glu Leu Ser Phe Gly Gln Phe Ala Ser Gln
            100                 105                 110

Gly Cys Leu Gly Val Trp Arg Ile Ser Pro Met Phe Lys Gly Val Gly
            115                 120                 125

Tyr Gly Met Met Val Val Ser Thr Tyr Ile Gly Ile Tyr Tyr Asn Val
            130                 135                 140

Val Ile Cys Ile Ala Phe Tyr Tyr Phe Phe Ser Ser Met Thr His Val
145                 150                 155                 160

Leu Pro Trp Ala Tyr Cys Asn Asn Pro Trp Asn Thr His Asp Cys Ala
                165                 170                 175

Gly Val Leu Asp Ala Ser Asn Leu Thr Asn Gly Ser Arg Pro Ala Ala
            180                 185                 190

Leu Pro Ser Asn Leu Ser His Leu Leu Asn His Ser Leu Gln Arg Thr
            195                 200                 205

Ser Pro Ser Glu Glu Tyr Trp Arg Leu Tyr Val Leu Lys Leu Ser Asp
            210                 215                 220

Asp Ile Gly Asn Phe Gly Glu Val Arg Leu Pro Leu Leu Gly Cys Leu
225                 230                 235                 240

Gly Val Ser Trp Leu Val Val Phe Leu Cys Leu Ile Arg Gly Val Lys
                245                 250                 255

Ser Ser Gly Lys Val Val Tyr Phe Thr Ala Thr Phe Pro Tyr Val Val
            260                 265                 270

Leu Thr Ile Leu Phe Val Arg Gly Val Thr Leu Glu Gly Ala Phe Asp
            275                 280                 285

Gly Ile Met Tyr Tyr Leu Thr Pro Gln Trp Asp Lys Ile Leu Glu Ala
            290                 295                 300

Lys Val Trp Gly Asp Ala Ala Ser
305                 310

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATGGCTGTGG CTCACGGACC TGTGG                                    25

(2) INFORMATION FOR SEQ ID NO:8:

-continued

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TGAAGACTTG ACTCCTCGAA TGAGGCAGAG                                              30
```